(12) United States Patent
Ince et al.

(10) Patent No.: US 8,936,939 B2
(45) Date of Patent: *Jan. 20, 2015

(54) HORMONE RESPONSIVE TISSUE CULTURE SYSTEM AND USES THEREOF

(75) Inventors: Tan A. Ince, Brookline, MA (US); Robert A. Weinberg, Brookline, MA (US)

(73) Assignees: Whitehead Institute for Biomedical Research, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/555,968

(22) Filed: Jul. 23, 2012

(65) Prior Publication Data

US 2013/0055417 A1 Feb. 28, 2013

Related U.S. Application Data

(63) Continuation of application No. 11/123,612, filed on May 6, 2005, now Pat. No. 8,252,591.

(60) Provisional application No. 60/569,005, filed on May 7, 2004, provisional application No. 60/630,934, filed on Nov. 24, 2004.

(51) Int. Cl.
*C12N 5/02* (2006.01)
*C12N 5/071* (2010.01)

(52) U.S. Cl.
CPC .................................... *C12N 5/0631* (2013.01)
USPC ........... 435/405; 435/325; 435/383; 435/384; 435/389; 435/406

(58) Field of Classification Search
None
See application file for complete search history.

(56) References Cited

U.S. PATENT DOCUMENTS

| | | | |
|---|---|---|---|
| 4,657,866 | A | 4/1987 | Kumar |
| 5,326,699 | A | 7/1994 | Torishima et al. |
| 5,405,772 | A | 4/1995 | Ponting |
| 5,443,954 | A | 8/1995 | Reddel et al. |
| 5,529,920 | A | 6/1996 | Cole et al. |
| 5,712,163 | A | 1/1998 | Parenteau et al. |
| 5,780,299 | A | 7/1998 | Coon et al. |
| 5,814,511 | A | 9/1998 | Chang et al. |
| 6,277,891 | B1 | 8/2001 | Sanders et al. |
| 6,383,805 | B1 | 5/2002 | Latimer |
| 6,451,601 | B1 | 9/2002 | Baetge et al. |
| 2002/0119565 | A1 | 8/2002 | Clarke et al. |
| 2004/0037815 | A1 | 2/2004 | Clarke et al. |
| 2005/0123521 | A1 | 6/2005 | Zern et al. |
| 2006/0019256 | A1 | 1/2006 | Clarke et al. |
| 2006/0252073 | A1 | 11/2006 | Yilmaz et al. |
| 2008/0299540 | A1 | 12/2008 | Ince et al. |

FOREIGN PATENT DOCUMENTS

| | | |
|---|---|---|
| EP | 1000541 A1 | 5/2000 |
| WO | WO/0073420 A2 | 12/2000 |

OTHER PUBLICATIONS

He et al., "Nucleotide, Supplements Alter Proliferation and Differentiation of Culture Human (Caco-2) and Rat (IEC-6) Intestinal Epithelial Cells," Biochemical and Molecular Roles of Nutrients, J. Nutr., vol. 123, pp. 1017-1027 (1993).
Al-Hajj et al., "Prospective identification of tumorigenic breast cancer cells." *Proc. Natl. Acad. Sci. U.S.A.* 100(7): 3983-8, 2003.
Bocker et al., "Common adult stem cells in the human breast give rise to glandular and myoepithelial cell lineages: a new cell biological concept." *Lab Invest.* 82(6): 737-46, 2002.
Boyce et al., "Calcium-regulated differentiation of normal human epidermal keratinocytes in chemically defined clonal culture and serum-free serial culture." *J Invest Dermatol.* 81(1 Suppl): 33s-40s, 1983.
Dick, "Breast cancer stem cells revealed." *Proc. Natl. Acad. Sci. U.S.A.* 100(7): 3547-9, 2003.
Dixon et al., Extracellular nucleotides stimulate proliferation in MCF-7 breast cancer cells via $P_2$-purinoceptors. British Journal of Cancer vol. 75, No. 1 pp. 34-39 (1997).
Elenbaas et al., "Human breast cancer cells generated by oncogenic transformation of primary mammary epithelial cells." *Genes Dev.* 15(1): 50-65, 2001.
Gudjonsson et al. "Isolation, immortalization, and characterization of a human breast epithelial cell line with stem cell properties." *Genes Dev.* 16(6): 693-706, 2002.
Ham's nutrient mixtures: Sigma-Aldrich, at the web- www.sigmaaltrich.com, see pp. 1- 13(print date Oct. 10, 2007).
Hammond et al., "Serum-free growth of human mammary epithelial cells: rapid clonal growth in defined medium and extended serial passage with pituitary extract." *Proc. Natl. Acad. Sci. U.S.A.* 81(17): 5435-9, 1984.

(Continued)

*Primary Examiner* — Satyendra Singh

(74) *Attorney, Agent, or Firm* — Foley Hoag LLP; David P. Halstead

(57) ABSTRACT

The invention provides tissue culture system for primary cells (e.g. normal mammalian primary epithelial progenitors). This system includes: a) a serum-free, chemically defined cell culture media; and, b) methods for isolation and in vitro long-term propagation of primary cells (e.g. primary epithelial cells). Primary cells so isolated and cultured can be kept undifferentiated and proliferate for many weeks (>15 weeks) or population doubling (>35 PD) without senescence, or any detectable genetic alterations. Upon changing media/culture conditions, these cells can be induced to differentiate. The invention also provides methods to transform normal primary cells so cultured into "cancer stem cells." The genetically defined cancer stem cell tumor model mimics the behavior of the disease closely, e.g., the cells are invasive, hormone responsive and metastatic when injected into mice. The tumor cells express genes that are specific to cancer stem cells identified in patient samples.

20 Claims, 10 Drawing Sheets
(10 of 10 Drawing Sheet(s) Filed in Color)

(56) References Cited

OTHER PUBLICATIONS

Iguchi T. et al. Growth of normal mouse vaginal epithelial cells in and on collagen gels, Proc. Natl. Acad. Sci., Jun. 1983, vol. 80, pp. 3743-3747.

Ince Tan A et al: "Transformation of different human breast epithelial cell types leads to distinct tumor phenotypes" Cancer Cell, vol. 12, No. 2, pp. 160-170 (2007).

J. Gregory Fitz. Regulation of Cellular ATP Release. Transactions of the American Clinical and Climatological Association. vol. 118, pp. 199-208 (2007).

John L. Gordon. Extracellular ATP: effects, sources and fate. Biochem. J. vol. 233 pp. 309-319 (1986).

Khakh et al., P2X receptors as cell-surface ATP sensors in health and disease. Nature vol. 422, No. 3, pp. 527-532 (2006).

Lechner J F et al: "A Serum-Free Method for Culturing Norman Human Bronchial Epithelialcells at Clonal Density" Journal of Tissue Culture Methods vol. 9, No. 2, pp. 43-48 (1995).

Lee et al., "Clonal expansion of adult rat hepatic stem cell lines by suppression of asymmetric cell kinetics (SACK)." *Biotechnol. Bioeng.* 83(7): 760-71, 2003.

Liu et al., "A Genetically Defined Model for Human Ovarian Cancer." *Cancer Res.* 64(5): 1655-1663, 2004.

Lundberg et al., "Immortalization and transformation of primary human airway epithelial cells by gene transfer." *Oncogene* 21(29): 4577-86, 2002.

Marx, "Cancer research. Mutant Stem Cells May Seed Cancer." *Science* 301(5638): 1308-10, 2003.

Matouskova et al., "Temporal in vitro expansion of the luminal lineage of human mammary epithelial cells achieved with the 3T3 feeder layer technique." *Breast Cancer Res. Treat.* 60(3): 241-9 2000.

Mustane et al., Autocrine Regulation of Volume-sensitive Anion Channels in Airway Epithelial Cells by Adensone* The Journal of Biological Chemistry vol. 271, No. 17, pp. 11701-11707 (1999).

Occhiuto et al., The phytoestrogenic isoflavones from *Trifolium pratense* L. (Red clover) protects human cortical neurons from glutamate toxicity. Phtomedicine vol. 15, Issue 9, pp. 676-682 (2008).

Paraskevi Moutsatou. The spectrum of phytoestrogens in nature: our knowledge is expanding. Hormones. vol. 6, No. 3, pp. 173-193 (2007).

Pechoux et al. "Human mammary luminal epithelial cells contain progenitors to myoepithelial cells." *Dev. Biol.* 206(1): 88-99, 1999.

Penttinen et al, Diet-Derived Polyphenol Metabolite Enterolactone Is a Tissue-Specific Estrogen Receptor Activator. Endocrinology. vol. 148, No. 10, pp. 4875-4886 (2007).

Print out from http://www.tocris.com/pharmacologicalBrowserphp?ItemId=80335. Last visited on May 5, 2010.

Print-out from www.cambrex.com/catnav.oid.692.prodoid.Mammedia (last visited on Aug. 25, 2006).

Print-out from www.cambrex.com/RelatedCatNav.catorg.17100.oid.534.prodoid.HMEC (last visited on Aug. 25, 2006).

Print-out from www.lbl.gov/LBL-Programs/mrgs/review.html#a4. (last visited on Aug. 25, 2006).

Rambhatla et al., "Cellular Senescence: Ex Vivo p53-Dependent Asymmetric Cell Kinetics." *J. Biomed. Biotechnol.* 1(1): 28-37, 2001.

Rangarajan et al., "Species and cell type-specific requirements for cellular transformation." *Cancer Cell.* 6(2):171-83, 2004.

Reigada et al., Degradation of extracellular ATP by the retinal pigment epithelium. Am. J. Physiol Cell Physiol vol. 289 pp. C617-C624 (2005).

Reya et al., "Stem cells, cancer, and cancer stem cells." *Nature* 414(6859): 105-11, 2001.

Sherley et al., "Asymmetric cell kinetics genes: the key to expansion of adult stem cells in culture." *Stem Cells* 20(6): 561-72, 2002.

Sherley et al., "Expression of the wild-type p53 antioncogene induces guanine nucleotide-dependent stem cell division kinetics." *Proc. Natl. Acad. Sci. U.S.A.* 92(1): 136-40, 1995.

Speirs et al., "Short-term primary culture of epithelial cells derived from human breast tumours." *Br. J. Cancer* 78(11): 1421-9, 1998.

Stampfer et al. "Culture systems for study of human mammary epithelial cell proliferation, differentiation and transformation." *Cancer Surv.* 18: 7-34, 1993.

Stampfer et al., "Human mammary epithelial cells in culture: differentiation and transformation." *Cancer Treat Res.* 40: 1-24, 1988.

Stingl et al. "Characterization of bipotent mammary epithelial progenitor cells in normal adult human breast tissue." *Breast Cancer Res. Treat.* 67(2): 93-109, 2001.

Wagner et al. "An adjunct mammary epithelial cell population in parous females: its role in functional adaptation and tissue renewal." *Development* 129(6): 1377-86, 2002.

Yang J. et al. "Sustained growth in primary culture of normal mammary epithelial cells embedded in collagen gels", Proc. Natl. Acad. Sci., USA, Apr. 1980, 77(4): 2088-2092.

Zhao et al. Neuroprotective and Neurotrophic Efficacy of Phytoestrogen in Cultured Hippocampal Neurons. Ex. Biol. Med. vol. 227, No. 7, pp. 509-519 (2002).

Richards et al. "Response of end bud cells from immature rat mammary gland to hormones when cultured in collagen gel," Exp Cell Res. 147:95-109 (1983).

Imagawa et al., "Serum-free Growth of Normal and Tumor Mouse Mammary Epithelial Cells in Primary Culture," Proceedings of the National Academy of Sciences of the USA, 79:407-44077 (1982).

Alkhalaf et al., "Proliferation of Guinea-Pig Uterine Epithelial Cells in Serum-Free Culture Conditions: Effect of 17b-Estradiol, Epidermal Growth Factor and Insulin," J. Steroid Biochem. Molec. Biol. 38(3):345-350 (1991).

Anantamongkol et al., "Prolactin and Dexamethasone Regulate Second Messenger-Stimulated CI—Secretion in Mammary Epithelia," Journal of Signal Transduction 1-15 (2012).

Suard et al., "Cell Proliferation and Milk Protein in Rabbit Mammary Cell Cultures," Journal of Cell Biology 96:1435-1442 (1983).

HORMONE RESPONSIVE TISSUE CULTURE SYSTEM AND USES THEREOF

RELATED APPLICATIONS

This application is a continuation of U.S. application Ser. No. 11/123,612, filed on May 6, 2005, now a U.S. Pat. No. 8,252,591 (issued on Aug. 28, 2012), which claims the benefit of the filing date of U.S. provisional application 60/569,005, entitled "Contribution of Target Cell Type to Epithelial Tumor Phenotypes," filed May 7, 2004 and U.S. provisional application 60/630,934, entitled "Hormone Responsive Tissue Culture System and Uses Thereof," filed Nov. 24, 2004. The entire teachings of the referenced applications are expressly incorporated herein by reference

GOVERNMENT SUPPORT

This invention was made with government support under Grant No. K08-CA-92013 awarded by the National Cancer Institute (NCI). The government has certain rights in the invention.

BACKGROUND OF THE INVENTION

Recent work comparing transformation and tumorigenicity of rodent and human cells has established significant differences between species. Therefore, it will be important to use human cells in creating tumor models that are relevant to human cancers.

SUMMARY OF THE INVENTION

The present invention provides a medium formulation, methods of making such media and methods of using such media to identify, isolate, or enrich primary cells and progenitor cells, and to proliferate such cells (e.g. normal primary mammary epithelial progenitors or stem cells, and other primary glandular epithelial cells, etc.).

The invention also provides methods of creating genetically defined tumor cells, including "tumor stem cells" that differentiate into metastatic adenocarcinomas.

A) Medium and Tissue Culture:

The medium of the present invention supports the growth of primary mammary epithelial progenitor cells that can give rise to a luminal epithelial phenotype and simultaneously suppresses the growth of other cell types. Thus, primary cells isolated using such a medium/system is essentially free of other cell types, especially those undesirable cell types, such as myoepithelial, stromal, and basal epithelial cell types.

Primary cells isolated and cultured using the methods and media of the invention can grow and proliferate in an undifferentiated state for many weeks (at least about 4 weeks, and usually more than about 15 weeks) or through many population doublings (PD; at least about 15 PD, usually more than 35 PD) without senescence or detectable genetic alterations. These cells can also be induced to undergo differentiation by changing media and culture conditions. In the case of mammary epithelial progenitors, the cells can differentiate in 3-D culture into epithelial cells of luminal phenotype characterized by luminal epithelial cell marker expression.

In a specific embodiment, the tissue culture medium of the invention is a chemically defined serum-free medium that is substantially free of animal serum and/or tissue or organ extracts (e.g. BPE).

As used herein, the term "serum-free" refers to the fact that the medium contains essentially no serum. In certain embodiments, there is 0% (completely free), or less than about 0.001%, 0.005%, 0.01%, 0.025%, or 0.05% total serum in the subject medium. The most common types of serums include: various forms of bovine serum (calf serum, fetal bovine serum, bovine calf serum, donor bovine calf serum, newborn bovine calf serum, etc.), horse serum and human serum.

"Chemically defined" means the structures, chemical formulae, and the percentage of the various individual components within a chemical composition are known or can be defined. Various tissue extracts, such as bovine pituatary extracts, are not chemically defined, at least partly because not all individual components of the extract are known. For those known components, the amount and the relative percentages of the various components could (and usually do) vary from one batch to another. This is partly caused by the fact that individual animals may have inherently different levels of various chemical compositions, even in the same tissue, depending on such factors a general health, nutrition, mood, pathological infections, trauma, etc.

In certain embodiments, the medium of the instant invention does not contain any animal serum products prepared for tissue culture purposes. Nor does it contain any tissue extracts with unknown/undefined chemical components. Instead, all essential components necessary to support the desired growth/proliferation of desired cell types are chemically defined. Most, if not all, of these individual components can be readily purchased as commercial products from various venders, such as Sigma-Aldrich Corp. (St. Louis, Mo.), GIBCO-Invitrogen Corp. (Carlsbad, Calif.); and BD Biosciences (San Jose, Calif.), etc.

In certain other embodiments, the presence in the subject medium of serum and/or tissue extracts, especially in trace amounts, would not substantially interfere with the characteristics of the medium, such as inhibiting the ability of the subject medium to support long-term undifferentiated cell growth and/or proliferation without a significant decrease in differentiation potential.

The invention also provides normal primary cells produced and/or isolated using the subject methods and media.

B) Transformation of Primary Cells and Creation of Tumor Xenografts:

The invention also provides methods to transform normal primary cells so cultured into engineered tumorigenic cells; when injected into immuno-compromised xenograph animals, the engineered tumorigenic cells are tumorigenic and recapitulate properties of breast cancer stem cells described in human tumors. In the case of mammary epithelial progenitor cells, more than 90% of the isolated cell population express CD44, CD24 and ESA (epithelial cell surface antigen). Upon transformation, more than 95% of the transformed cells express CD44, CD24 and ESA and the number (e.g., about 1000) of such transformed cells that need to be injected into immuno-compromised xenographic animals to generate tumors in about 50% of the injected animals is less than that needed using presently-available techniques. This number of cells is about 1000-fold lower than the number of tumor cells needed in a traditional xenographic transplantation.

In tumor cells isolated from such xenographic animals, a mixed population of tumor cells with mixed $CD44^{+/-, ESA+/-}$ and $CD24^{+/-}$ expression is obtained. When tissue culture cells or tumor cells isolated from explanted tumors are isolated, separated into $CD44^+$, $CD44^-$, $CD24^+$ and $CD24^-$ fractions, and reinjected into nude mice, only $CD44^+$ and $CD24^-$ fractions are capable of forming tumors, which is consistent with the tumor stem cell hypothesis that a small population of highly tumorigenic tumor stem cells can regenerate themselves and produce other low tumorigenic tumor cells. In addition, this genetically defined cancer stem cell tumor model mimics the behavior of the disease closely. For example, the tumorigenic cells are invasive, hormone responsive, and metastatic when injected into xenographic animals. The tumor cells also express gene products that are specific to cancer stem cells identified in patient samples.

Thus, the invention also provides transformed primary cells that are tumorigenic in immuno-compromised animals. Such transformed cells are useful for establishing a tumor model that mimics characteristics of cancer or tumors as they occur in vivo, in terms of invasiveness, hormone responsiveness and metastasis.

The invention also provides such a tumor model and the use of the tumor cells and tumor models in methods of screening for candidate drugs or drug leads specifically targeting stem cell-like cancer cells. While previous work identified tumor stem cells in patient samples, no methods of in vitro expansion of these cells were developed. Therefore, to our knowledge our system is the only one in which in vitro drug screening is possible in human tumor stem cells and their normal counterparts.

The tumorigenic cells and tumor models of the invention can be further used to compare various characteristics of relatively normal cells (e.g., their parent primary cells) and the derived tumorigenic cells, both in vitro and in vivo. In theory, any characteristics that can be measured or studied can be compared between these two cell populations. For illustration only, and without limitation, these include the following properties/behavior/characteristics of the cells: growth, proliferation, potential to invade or metastasize, anchorage-independent growth, cell cycle progression, apoptosis, senescence, drug resistance, immunogenicity, sensitivity to chemo-/radiotherapy, differentiation potential, expression of various markers, etc.

The invention also provides a method to carry out a pharmaceutical/biotechnology business, comprising establishing a tumor model of primary cells isolated using the media and methods of the instant invention, and screening for drug molecules or drug leads specifically or preferentially targeting such tumors. The business method may further include licensing the rights to such tumor cell/tumor model/drug candidates to third party. The business method may further comprise marketing of such established tumor cells/tumor models for sale or licensing.

Thus, one aspect of the invention relates to a culture medium comprising: (1) one or more lipid synthesis precursors; (2) one or more protein synthesis precursors (at least the essential amino acids, optionally also including non-essential amino acids); (3) one or more carbohydrate synthesis precursors and energy metabolism precursors; (4) one or more cations (e.g. monovalent and divalent), ions, trace metals and enzyme cofactors/vitamins; (5) one or more agents that induce increased intracellular 3'-5' cyclic adenosine monophosphate (cAMP) levels; and, (6) insulin, wherein the medium supports undifferentiated growth and/or proliferation of primary breast epithelial progenitor cells for at least about 4 weeks or at least about 15 population doubling (PD) in vitro, without a significant decrease in differentiation potential.

In another embodiment, the invention relates to a culture medium comprising: (1) one or more lipid synthesis precursors; (2) one or more protein synthesis precursors; (3) one or more carbohydrate synthesis and energy metabolism precursors; (4) one or more monovalent and/or divalent cations, ions, trace metals and enzyme cofactors/vitamins; and, (5) insulin, wherein the medium supports undifferentiated growth and/or proliferation of primary breast epithelial progenitor cells transformed by telomerase catalytic subunit (e.g. hTERT) for at least about 4 weeks or at least about 15 population doubling (PD) in vitro, without a significant decrease in differentiation potential.

Energy metabolism precursors are usually carbohydrates; they may overlap with carbohydrate synthesis precursors, such as glucose. However, since amino acids and lipids may also be energy metabolism precursors, such composition may also overlap with lipid synthesis precursors and/or protein synthesis precursors.

Many enzymes use cofactors (e.g. nonprotein component of enzymes). If the cofactor is organic, then it is called a coenzyme. Many of the coenzymes are derived from vitamins, including vitamins A, B1 (thiamin), B12, D, E, K, and forlic acid. Other enzyme cofactors include niacin, pantothenic acid, and riboflavin, etc.

In certain embodiments, the medium also comprises one or more of the following: (1) one or more antioxidants; (2) one or more nucleotide salvage pathway synthesis precursors; (3) one or more buffers; (4) one or more carrier proteins (such as bovine serum albumin); (5) one or more detergents (such as Tween80); (6) one or more non-insulin hormones and growth factors.

In certain embodiments, the medium supports growth and/or proliferation of primary breast epithelial progenitor cells without detectable genetic alterations. In certain embodiments, the genetic alteration is p16 inactivation. In certain embodiments, the medium does not support survival or sustained growth or proliferation of fibroblasts and breast stromal cells. In certain embodiments, the medium supports growth and/or proliferation of cells which are substantially free of expression of stress indicator genes, such as p53 and/or p16. In certain embodiments, the medium is substantially free of at least one member selected from the group consisting of: serum, heparin, fibroblast growth factor (FGF), and bovine pituatary extract (BPE). In certain embodiments, the medium supports growth and/or proliferation of cells which are substantially free of expression of epithelial differentiation markers and mesenchymal differentiation markers. In certain embodiments, the epithelial differentiation markers comprise at least one member selected from the group consisting of: keratin 8, keratin 10, keratin 14, keratin 18, keratin 19, E-cadherin, p63, smooth muscle actin (SMA), and β-catenin. In certain embodiments, the mesenchymal differentiation marker is vimentin.

In certain embodiments, the one or more antioxidants comprise at least one antioxidant selected from the group consisting of: glutathione (reduced), dithiothreitol (DTT), vitamin E, vitamin K3, vitamin D2 or calciferol, niacin, niacinamide, and ascorbic acid. In certain embodiments, the one or more nucleotide salvage pathway synthesis precursors are selected from the group consisting of: hypoxanthine, xanthine, adenine, guanine, and thymidine. In certain embodiments, the one or more lipid synthesis precursors are selected from the group consisting of: cholesterol, linoleic acid, lipoic acid, and o-phosphoryl ethanolamine. In certain embodiments, the one or more hormones are selected from the group consisting of: progesterone, testosterone, hydrocortisone, and estrogen. In certain embodiments, the one or more growth factors are selected from the group consisting of: insulin and epidermal growth factor (EGF). In certain embodiments, the agents that induce increased intracellular cAMP levels directly increase intracellular cAMP levels. In certain embodiments, the one or more agents that induce(s) increased intracellular cAMP levels inhibit a cAMP phosphodiesterase. In certain embodiments, the one or more agents that induce(s) increased intracellular cAMP levels are selected from the group consisting of: a β-adrenergic receptor agonist, dibutyryl cAMP, isobutylmethylxanthine, theophylline, isoproterenol, cholera toxin and forskolin.

In certain embodiments, the medium further comprises at least one buffer, such as N-[2-hydroxyethyl]piperazine-N'-[2-ethanesulfonic acid] (HEPES) buffer, sodium bicarbonate buffer, or a combination of both.

In certain embodiments, the medium comprises the components listed in Table II. In a specific embodiment, the medium includes the components listed in Table II, each present in the concentration shown or within the listed concentration range. In other embodiments, the medium includes the components listed in Table II, with at least one of the components present at a concentration that is about 5%, 10%, 20%, 50%, 100% higher or lower than the listed maximum or minimum concentration.

In certain embodiments, the medium comprises about 50% Medium 199 (M199) and about 50% F12 (Ham) medium, supplemented with glutamine, EGF, transferrin, insulin, progesterone, testosterone, 17B-estradiol, o-phosphorylethanolamine, selenious acid, lionleic acid, BSA, triiodothyronine, hydrocortizone, cholera toxin, HEPES, and other components to approximately their corresponding concentrations as listed in Table II.

In certain embodiments, the medium supports undifferentiated growth and/or proliferation of primary breast epithelial progenitor cells transfected with telomerase, for at least about 15 months in vitro, without a substantial decrease in differentiation potential.

In certain embodiments, the medium supports growth, proliferation, and/or differentiation of primary breast epithelial progenitor cells induced to express: (1) telomerase catalytic subunit, (2) a first polypeptide that functions in the same signaling pathway(s) as the SV40 large T antigen, and (3) a second polypeptide that functions in the same signaling pathway as the mutant H-ras oncogene product, for at least about 15 weeks or at least about 35 population doubling (PD) in vitro, without losing tumorigenicity.

In certain embodiments, the medium comprises the components listed in Table I. In certain embodiments, the medium comprises about 50% Medium 199 (M199) and about 50% F12 (Ham) medium, supplemented with glutamine, EGF, transferrin, insulin, 17β-estradiol, o-phosphorylethanolamine, selenious acid, lionleic acid, BSA, triiodothyronine, hydrocortizone, cholera toxin, and HEPES, to approximately their corresponding concentrations listed in Table I. In certain embodiments, the medium further comprises one or more antibiotics, such as penicillin and/or streptomycin. In certain embodiments, the medium is a 1×medium formulation, or a concentrated medium formulation of about 2×, 5×, or 10×formulation. In certain embodiments, at least some components of the medium is a concentrated formulation of about 2×, 5×, 10×, 100×, or 1000×. In certain embodiments, at least some or all components of the medium are in liquid/aqueous form. In certain embodiments, at least some or all components of the medium is in solid, powder, or frozen form.

In certain embodiments, the medium supports the growth, proliferation, and/or differentiation of mammalian cells. In certain embodiments, the mammalian cells are non-human mammalian cells. In certain embodiments, the non-human mammalian cells are from mouse, rat, non-human primate (e.g. monkey), rabbit, dog, or cat. In certain embodiments, the medium supports the growth, proliferation, and/or differentiation of cells from normal glandular epithelial cells of an organ/tissue selected from: breast, prostate, ovary, pancreas, stomach, intestine, colon, endocervix, kidney, skin, lung, uterus, parotid gland, or fallopian tube. In certain embodiments, the medium supports the growth, proliferation, and/or differentiation of endometrial cells or cervical cells. In certain embodiments, the medium supports the differentiation of breast glandular epithelial cells to luminal phenotype, but not basoid phenotype. In certain embodiments, the luminal phenotype is characterized by specific keratin expression profiles typical of luminal mammary epithelial cells. In certain embodiments, the medium is substantially free of bovine pituatary extract (BPE), or other tissue/organ extracts with undefined chemical composition. In certain embodiments, the medium supports undifferentiated growth and proliferation of the cells for at least about 5, 6, 7, 8, 9, 10, 11, 12, 13, 14, or 15 weeks in culture. In certain embodiments, the medium supports undifferentiated growth and proliferation of a population of breast progenitor cells characterized by expression of CD44, CD24, and ESA in >85% of the cells.

Another aspect of the invention provides a composition comprising solid form chemicals which, when dissolved in an aqueous solvent, produce a culture medium described or claimed herein.

The invention further relates to a method of isolating mammalian primary cells, comprising: (a) providing tissues containing the primary cells from a mammal; (b) separating or enriching the primary cells from other cells in the tissues; (c) plating the primary cells produced in (b) on a tissue culture container with mixed (+/−) charge surface, in the subject medium for about a week with frequent (e.g. daily) medium change; (d) harvesting the primary cells by using high concentration of trypsin at about 0.15%, and transferring the harvested the primary cells to a new tissue culture container with mixed (+/−) charge surface in the subject medium, thereby isolating the primary cells from the mammal.

In certain embodiments, the method further comprises, before (d), removing residual cells other than the primary cells by selective trypsin digestion using low concentration of trypsin at about 0.025%, over a period of 1-3 days.

In certain embodiments, the primary cells are primary glandular epithelial cells.

In certain embodiments, the tissues are from: breast, prostate, ovary, pancreas, stomach, intestine, colon, endocervix, kidney, skin, lung, uterus, parotid gland, or fallopian tube.

In certain embodiments, the other cells are stromal cells and/or myoepithelial cells.

In certain embodiments, step (b) is effectuated by collagenase digestion of the tissues overnight at 37° C., followed by three consecutive rounds of centrifugation for 5 minutes each at 300×g, 100×g, and 50×g, respectively.

In certain embodiments, the tissue culture container is a PRIMARIA™ container made from surface-modified polystyrene.

Another aspect of the invention provides a primary cell isolated using the method of the invention, wherein the primary cells grow and/or proliferate in the subject medium for at least about 4 weeks or at least about 15 population doubling (PD) in vitro, without any detectable genetic alterations, or losing differentiation potential.

In certain embodiments, the primary cell is a primary glandular epithelial cell.

In certain embodiments, the primary glandular epithelial cell is from a tissue/organ selected from: breast, prostate, ovary, pancreas, stomach, intestine, colon, endocervix, kidney, skin, lung, uterus, parotid gland, or fallopian tube.

In certain embodiments, the primary cell grows and/or proliferates in the subject medium for at least about 15 weeks or at least about 35 population doubling (PD) in vitro.

In certain embodiments, the genetic alterations comprise p16 inactivation.

In certain embodiments, the primary cell is substantially free of fibroblasts and stromal cells.

In certain embodiments, the primary cell is substantially free of stress gene (e.g. p16, p53) expression.

In certain embodiments, the primary cell is substantially free of epithelial differentiation markers expression and mesenchymal differentiation markers expression.

In certain embodiments, the primary cell is hormone responsive before and during culturing in the medium.

The invention further relates to a tumorigenic cell derived from the subject primary cell, wherein the tumorigenic cell expresses: (1) a telomerase catalytic subunit; (2) a first polypeptide functions in the same signaling pathway(s) as does the SV40 large T antigen; and, (3) a second polypeptide functions in the same signaling pathway as does the mutant H-ras oncogene product. Optionally, the tumorigenic cell also expresses SV40 small t antgen, or has diminished level of target proteins of the small t antigen in the cell (such as PP2A etc.) The diminished level of SV40 large and/or small t antigens may be brought about by any means, including siRNA or antibody against the target protein(s). The function of SV40 large T antigen may also be replaced by HPV E6 and E7 proteins.

In certain embodiments, about 1000 of the subject cell, when injected into each xenograph animals, generate tumors in at least about 40-50% of the animals.

In certain embodiments, the tumorigenic cells are at least about 88% $CD44^+$, $CD24^+$, and $ESA^+$, and have essentially no vimentin expression.

In certain embodiments, the tumorigenic cell, which generates tumors in a xenograph animal, gives rise to a mixed population of tumor cells with mixed expression of CD44, CD24, ESA, vimentin, E-cadherin, or keratin 18. In certain embodiments, xenograph tumors arising from the injected tumorigenic cells form glandular structures similar to those seen in human tumors. In certain embodiments, xenograph tumors arising from the injected tumorigenic cells are invasive into adjacent tissues, such as skeletal muscle. In certain embodiments, xenograph tumors arising from the injected tumorigenic cells are metastatic. In certain embodiments, xenograph tumors arising from the injected tumorigenic cells metastasize to lung in >95% of the host xenograph animals.

In certain embodiments, xenograph tumors arising from the injected tumorigenic cells express at least one of progesterone, testosterone, and/or estrogen receptors, and are responsive to treatment with at least one of progesterone, testosterone, and/or estrogen.

Another aspect of the invention provides a method of subculturing isolated primary cells from a mammal, the method comprising: (1) harvesting isolated and cultured primary cells by using high concentration of trypsin from about 0.075% to about 0.15%, (2) resuspending harvested the primary glandular epithelial cells in the subject medium supplemented with a trypsin inhibitor; (3) plating the resuspended primary glandular epithelial cells on a tissue culture container with mixed (+/−) charge surface; (4) replacing the medium with fresh subject medium, as soon as the primary glandular epithelial cells have attached to the surface of the tissue culture container.

In certain embodiments, the primary cells are primary glandular epithelial cells.

In certain embodiments, the trypsin inhibitor is about 5% calf serum (CS).

Another aspect of the invention provides a method for long-term culturing and maintenance of hormone-responsive primary cells from a mammal, the method comprising: (1) isolating primary cells from the mammal using the subject method; (2) using the subject method to culture and subculture the primary cells isolated in (1) in the subject medium.

In certain embodiments, the primary cells are primary glandular epithelial cells.

In certain embodiments, the method further comprises introducing ectopic genetic materials into the hormone-responsive primary cells or primary glandular epithelial cells.

In certain embodiments, the method further comprises stimulating the primary cells or the primary glandular epithelial cells with one or more hormone(s).

In certain embodiments, the method further comprises contacting the hormone-responsive glandular epithelial cells with one or more drug(s) or drug candidate(s).

Another aspect of the invention provides a method for inducing differentiation of isolated mammary epithelial progenitor cells to epithelial cells of luminal phenotype, comprising: (1) isolating and culturing the mammary epithelial progenitor cells according to the subject method; (2) inducing the differentiation of the mammary epithelial progenitor cells to epithelial cells of luminal phenotype.

In certain embodiments, step (2) of the method is effectuated by culturing cells in 3-D culture with EHS.

In certain embodiments, the differentiation is characterized by expression of markers specific for luminal phenotype.

In certain embodiments, the markers include one or more of: keratin 8, keratin 18, E-cadherin, and β-catenin.

The invention also relates to a kit for isolating and culturing glandular epithelial cells from a mammal, the kit comprising a carrier means having in close confinement therein one or more container means: (1) wherein a first container means contains any of the subject medium; (2) an instruction for isolating and subculturing glandular epithelial cells from the mammal.

In certain embodiments, the kit further comprises collagenase and/or trypsin.

In certain embodiments, the collagenase is supplied in Hank's buffered saline solution (HBSS).

In certain embodiments, the trypsin is supplied in a high concentration of about 0.075% -0.15% and a low concentration of about 0.025%.

The invention also relates to a kit for isolating and culturing glandular epithelial cells from a mammal, the kit comprising a carrier means having in close confinement therein one or more container means: (1) wherein a plurality of the container means each individually contain, in proportion, solid forms of the components for any of the subject medium, such as that listed in Table II; (2) an instruction for making any one of the subject medium; (3) an instruction for isolating and subculturing glandular epithelial cells from the mammal.

In certain embodiments, at least some of the components of the kit are stored at different temperatures as that for other of the components.

In certain embodiments, at least some of the components of the kit are stored as liquid.

In certain embodiments, at least some of the components of the kit are stored as solid powder.

In further embodiments, the invention relates to a method for in vitro comparison of the characteristics of normal glandular epithelial cells and abnormal glandular epithelial cells derived therefrom, comprising: (1) isolating normal (primary) glandular epithelial cells using the subject method; (2) culturing the isolated normal glandular epithelial cells under the same condition as that of the abnormal (e.g. genetically modified, in tumor or genetic transformation) glandular epithelial cells; (3) comparing the behavior of the normal glandular epithelial cells and abnormal glandular epithelial cells.

In certain embodiments, the condition includes treatment by a hormone to which the normal glandular epithelial cells respond.

In certain embodiments, the abnormal glandular epithelial cells are derived from the normal glandular epithelial cells by introducing one or more ectopic genes therein.

In certain embodiments, the ectopic genes include: (1) a telomerase catalytic subunit; (2) a first polypeptide functions in the same signaling pathway(s) as does the SV40 large T antigen; and, (3) a second polypeptide functions in the same signaling pathway as does the mutant H-ras oncogene product.

In certain embodiments, the abnormal glandular epithelial cells are derived from a tumor/cancer/diseased tissue from which the normal glandular epithelial cells are obtained.

Another aspect of the invention provides a method of producing tumorigenic cells from corresponding normal primary cells, the method comprising: (1) isolating normal primary cells using the subject method; (2) introducing into the isolated cells exogenous DNA which, when expressed in the isolated cells, transforms the cells into tumorigenic cells which form tumors in immunocompromised mice into which they are introduced.

In certain embodiments, the exogenous DNA comprises: (a) DNA that encodes human telomerase catalytic subunit; (b) DNA that encodes a first oncogene or inhibitor of a first tumor suppressor (TS) gene; and, (c) DNA that encodes a second oncogene or inhibitor of a second TS gene, wherein the first oncogene/the first TS gene and the second oncogene/second TS gene function in two distinct biochemical pathways in human somatic cells.

In certain embodiments, the DNA of (a) is cDNA which encodes human telomerase catalytic subunit; the DNA of (b) is cDNA that encodes a first oncogene; and the DNA of (c) is cDNA that encodes a second oncogene, wherein the first oncogene and the second oncogene function in two distinct biochemical pathways in primary cells.

In certain embodiments, the biochemical pathways are signaling pathways and the cDNA of (b) encodes an oncogene which functions in the same signaling pathway as does the ras oncogene product, and the cDNA of (c) encodes an oncogene which functions in the same signaling pathways as does the SV40 LT antigen oncoprotein, wherein function of the oncogene encoded by the cDNA of (b) and function of the oncogene encoded by the cDNA of (c) in their respective signaling pathways in the normal human somatic cells in which human telomerase catalytic subunit is ectopically expressed results in production of tumorigenic human somatic cells.

In certain embodiments, the DNA of (b) is cDNA that encodes the H-ras oncogene product, and the DNA of (c) is cDNA that encodes the SV40 large T oncogene product.

In certain embodiments, the tumorigenic human somatic cells produced from tumors in immunocompromised mice into which they are introduced and the tumors formed are invasive and/or metastatic in the mice.

Another aspect of the invention provides a tumorigenic cell produced by the subject method. In certain embodiments, the tumorigenic cell is a human cell.

Another aspect of the invention provides an in vitro method of identifying a drug which reduces proliferation of tumorigenic cells, comprising: (1) propagating the subject tumorigenic cells, or tumorigenic cells produced by the subject method, in the presence of a candidate drug to be assessed for its ability to reduce proliferation of the tumorigenic cells, under conditions appropriate for the drug to enter cells; (2) determining the extent to which proliferation of the tumorigenic cells occurs in the presence of the candidate drug to be assessed; and, (3) comparing the extent determined with the extent to which proliferation of the tumorigenic cells occurs under the same conditions, but in the absence of the candidate drug to be assessed, wherein if proliferation occurs to a lesser extent in the presence of the candidate drug to be assessed than in its absence, the candidate drug to be assessed is a drug which reduces proliferation of tumorigenic human somatic cells. In certain embodiments, the tumorigenic cells form a tumor in an immunocomprimised xenographic animal model. In certain embodiments, the tumor is invasive and/or metastatic.

Another aspect of the invention provides an in vitro method of identifying a drug which inhibits or negatively affects one or more characteristics of tumorigenic cells, the characteristics including: cell viability, growth, proliferation, invasiveness, ability to metastasize, anchorage-independent growth, or angiogenesis, the method comprising: (1) propagating the subject tumorigenic cells, or tumorigenic cells produced by the subject method, in the presence of a candidate drug to be assessed for its ability to inhibit or negatively affect the one or more characteristics of the tumorigenic cells, under conditions appropriate for the drug to enter cells; (2) determining the extent to which the characteristics is inhibited or negatively affected in the presence of the candidate drug to be assessed; and, (3) comparing the extent determined with the characteristics of the tumorigenic cells under the same conditions, but in the absence of the candidate drug to be assessed, wherein if the characteristics is substantially inhibited or negatively affected in the presence of the candidate drug to be assessed than in its absence, the candidate drug to be assessed is a drug which inhibits or negatively affects one or more the characteristics of the tumorigenic cells.

In certain embodiments, the one or more characteristics is inhibited or negatively affected by at least about 20%, 40%, 50%, 60%, 70%, 80%, 90%, or 100% in the presence of the candidate drug to be assessed than in its absence.

In certain embodiments, the method further comprises using the identified drug as a lead molecule to identify additional drugs that more potently inhibit or negatively affect the characteristics. Another aspect of the invention provides a drug identified by the subject method. Another aspect of the invention provides a pharmaceutical composition comprising an effective amount of the subject drug, and one or more pharmaceutically acceptable excipient or salt.

Another aspect of the invention provides an in vitro method of identifying a drug which enhances or positively affects one or more characteristics of tumorigenic cells, the characteristics including: differentiation, apoptosis, sensitivity to chemotherapy/radiotherapy, or senescence, the method comprising: (1) propagating the subject tumorigenic cells, or tumorigenic cells produced by the subject method, in the presence of a candidate drug to be assessed for its ability to enhance or positively affect the one or more characteristics of the tumorigenic cells, under conditions appropriate for the drug to enter cells; (2) determining the extent to which the characteristics is enhanced or positively affected in the presence of the candidate drug to be assessed; and, (3) comparing the extent determined with the characteristics of the tumorigenic cells under the same conditions, but in the absence of the candidate drug to be assessed, wherein if the characteristics is substantially enhanced or positively affected in the presence of the candidate drug to be assessed than in its absence, the candidate drug to be assessed is a drug which enhances or positively affects one or more the characteristics of the tumorigenic cells.

Another aspect of the invention provides an in vivo method of identifying a drug which inhibits or negatively affects one or more characteristics of tumor generated by tumorigenic cells in a tumor model, the characteristics including: tumor growth, invasiveness, metastasis, or angiogenesis, the method comprising: (1) introducing to test animals the subject tumorigenic cells, or tumorigenic cells produced by the subject method, to generate tumors; (2) administering a candidate drug to the test animals to assess its ability to inhibit or negatively affect the one or more characteristics of the tumor; and, (3) determining the extent to which the characteristics is inhibited or negatively affected in the presence of the candidate drug; wherein if the characteristics is substantially inhibited or negatively affected in the presence of the candidate drug to be assessed than in its absence, the candidate drug to be assessed is a drug which inhibits or negatively affects one or more the characteristics of the tumor.

Another aspect of the invention provides a method of identifying a gene whose expression in a tumorigenic cell is related to/involved in metastasis of such cells in vivo, comprising: (1) introducing a candidate gene into the subject tumorigenic cells, or tumorigenic cells produced by the subject method, thereby producing modified tumorigenic cells; (2) introducing the modified tumorigenic cells to test animals; (3) maintaining the test animals under conditions appropriate for formation of tumors and metastasis to occur; and (4) determining whether metastasis of the modified tumorigenic cells occurs, wherein, if metastasis occurs, the candidate gene is a gene whose expression in a tumorigenic cell is related to/involved in metastasis of such cells in vivo.

Another aspect of the invention provides a method of identifying a gene whose expression in a tumorigenic cell is related to/involved in invasion of such cells in vivo, comprising: (1) introducing a candidate gene into the subject tumorigenic cells, or tumorigenic cells produced by the subject method, thereby producing modified tumorigenic cells; (2) introducing the modified tumorigenic cells to test animals; (3) maintaining the test animals under conditions appropriate for formation of tumors and invasion to occur; and (4) determining whether invasion of the modified tumorigenic cells occurs, wherein, if invasion occurs, the candidate gene is a gene whose expression in a tumorigenic cell is related to/involved in invasion of such cells in vivo.

Another aspect of the invention provides a method of identifying a gene product which is expressed in tumor cells but not in normal cells of the same type, or a gene product which is not expressed in tumor cells but is expressed in normal cells of the same type, comprising: (1) analyzing the subject tumorigenic cells, or tumorigenic cells produced by the subject method; (2) analyzing normal parental cells of which the tumorigenic cells are a variant for gene products; and, (3) comparing gene products produced by the tumorigenic cells and the normal parental cells, whereby a gene product which is expressed in tumorigenic cells but not in normal parental cells, or a gene product which is not expressed in tumorigenic cells but is expressed in normal parental cells is identified, thereby identifying a gene product which is expressed in tumor cells but not in normal cells of the same type, or a gene product which is not expressed in tumorigenic cells but is expressed in normal cells of the same type.

BRIEF DESCRIPTION OF THE DRAWINGS

The application file contains at least one drawing executed in color. Copies of this application publication with color drawing(s) will be provided by the U.S. Patent and Trademark Office upon request and payment of the necessary fee.

DETAILED DESCRIPTION OF THE INVENTION

I. Formulation of Culture Media

Figure 1:
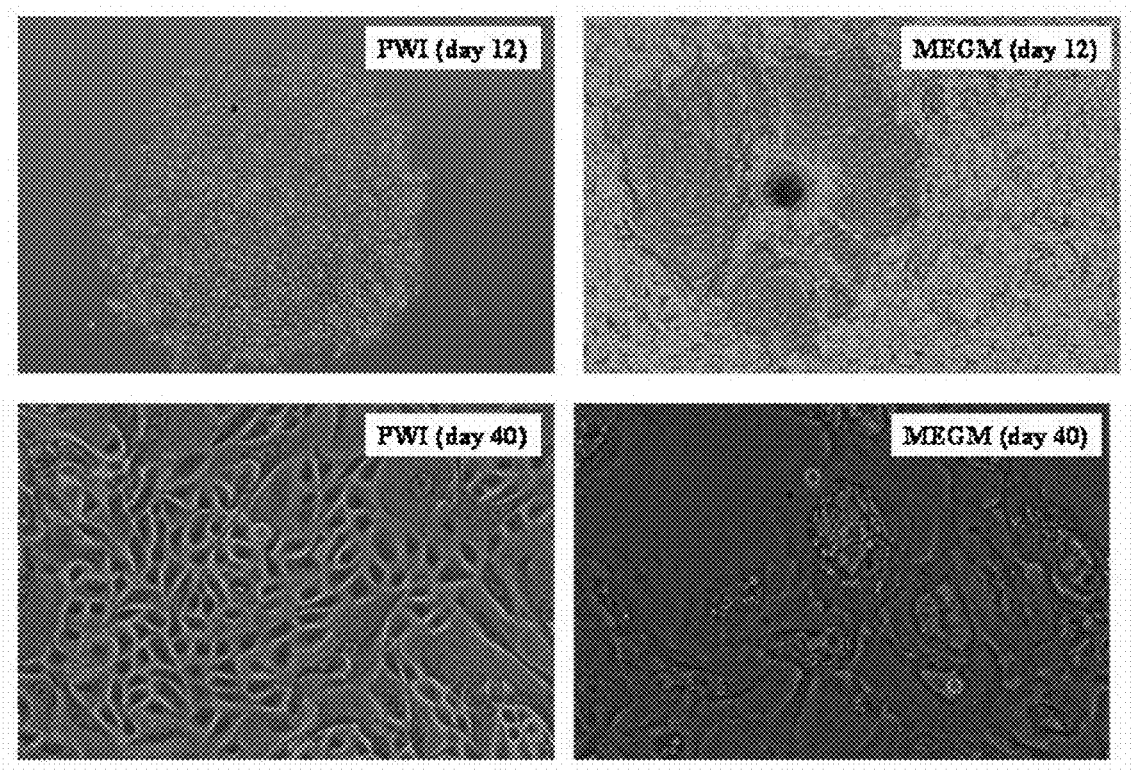
FIG. 1 illustrates that on day 12, while primary organoid cultures result in homogenous uniform colonies in the subject medium (e.g. PWI), there are multiple cell types forming a bi-phasic appearance in MEGM. Moreover, on day 40, cells in PWI are small and proliferating. But in MEGM medium, the cells have the typical flat, enlarged, and vacuolated appearance of senescent cells.

The subject invention relates to a medium that supports long-term, undifferentiated, growth and proliferation of primary cells (including primary mammalian epithelial cells) in vitro. In a specific embodiment, such medium is essentially free of serum, tissue/organ extracts, FGF, heperan, etc. In certain embodiments, FGF final concentration in the subject medium is less than about 0.0001 mg/L, about 0.001 mg/L, or about 0.005 mg/L. The phrases "cell culture medium," "culture medium" (plural "media" in each case) and "medium formulation" refer to a nutritive solution for cultivating cells and may be used interchangeably.

In one embodiment, such primary mammalian epithelial cells can grow for at least 4 weeks (or 15 population doublings), up to several months, in such a culture medium without losing differentiation potential. In a specific embodiment, the subject medium supports long-term undifferentiated growth and proliferation of primary breast epithelial cells transfected with telomerase, for at least about 15 weeks or at least about 35 population doubling (PD) in vitro, without any additional detectable genetic alterations, or losing differentiation potential. In another embodiment, the subject medium supports undifferentiated growth and proliferation of primary cells for at least 5, 6, 7, 8, 9, 10, 11, 12, 13, 14, 15 weeks or more in culture.

The cell culture media of the present invention are aqueous-based (but can be reconstituted from dry powder and/or frozen components), comprising a number of ingredients in a solution of deionized, distilled water.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

In one embodiment, the tissue culture medium of the invention comprises: (1) one or more antioxidants; (2) one or more nucleotide salvage pathway synthesis precursors; (3) one or more lipid synthesis precursors; (4) one or more protein synthesis precursors; (5) one or more carbohydrate synthesis and energy metabolism precursors; (6) one or more buffers (not essential); (7) one or more cations (monovalent and/or divalent), ions, trace metals and enzyme cofactors; (8) one or more carrier proteins (such as bovine serum albumin); (9) one or more detergents (such as tween80); (10) one or more agents that induce increased intracellular 3'-5' cyclic adenosine monophosphate (cAMP) levels; and/or (11) one or more hormones and growth factors, wherein the medium supports undifferentiated growth and/or proliferation of primary breast epithelial progenitor cells for at least about 4 weeks or at least about 15 population doubling (PD) in vitro, without a significant decrease in differentiation potential. An example of such medium is illustrated below in Table II.

In other embodiments, one or more of the above-listed categories of components may be omitted, provided that the resulting medium supports undifferentiated growth and/or proliferation of primary breast epithelial progenitor cells for at least about 4 weeks or at least about 15 population doubling (PD) in vitro, without a significant decrease in differentiation potential.

Thus, the medium of the invention comprises one or more antioxidants; nucleotide synthesis and salvage pathway precursors; lipid synthesis precursors; agonists of intracellular cAMP level; and, hormones and growth factors. The medium may additionally comprise other components such as amino acid supplements, vitamins necessary for cell growth/proliferation, trace minerals, inorganic salts, energy sources (e.g. for glycolysis), and other components such as pH indicators, etc. In other words, ingredients of the present invention may include amino acids, vitamins, inorganic salts, adenine, D-glucose, N-[2-hydroxyethyl]piperazine-N'-[2-ethanesulfonic acid] (HEPES), hydrocortisone, insulin, lipoic acid, phenol red, phosphoethanolamine, putrescine, sodium pyruvate, triiodothyronine (T3), thymidine and transferrin. Each of these ingredients may be obtained commercially, for example from Sigma (Saint Louis, Mo.).

While not wishing to be bound by any particular theory, antioxidants generally help to quench free-radicals, which are thought to be detrimental to cell growth in general. The antioxidants of the invention may include, without limitation, one or more of the following: beta-carotene, vitamin E, vitamin C (ascorbic acid), vitamin K3, glutathione (reduced), niacin (or niacinamide), or DTT (dithiothreitol). The antioxidants may optionally be supplemented with trace metals, including Zn, Se, Cr, Cu, Mg, or Mn.

Again, without wishing to be bound by theory, trace minerals may be necessary for the constitution of certain enzymes. For example glutathione peroxidase uses selenium and glutathione superoxide uses copper as a cofactor. It was postulated that in diseases where there is a large free radical load, there may be deficiencies of these trace elements in a particular microenvironment. The presence of trace minerals may be helpful to enzymatic antioxidants (which may have been devoid of the cofactors). Thus the presence of the trace minerals may allow effective use of the enzymatic antioxidants by the host. Since it is known that zinc can up-regulate superoxide dismutase and selenium can up-regulate glutathione peroxidase, increasing trace minerals in a given microenvironment would produce a net increase in enzymatic antioxidants in the microenvironment. A net increase in the enzymatic antioxidants and increasing amphipathic antioxidant would further reduce oxidative damage to tissue or cells, as well as other deleterious effects due to free radicals.

Thus many inorganic salt ingredients, cations, ions, trace metals, and vitamins, which may be beneficial in the media of the present invention include a calcium salt (e.g., $CaCl_2$), $CuSO_4$, $FeSO_4$, KCl, a magnesium salt (e.g., $MgCl_2$), Sodium acetate, NaCl, $NaHCO_3$, $Na_2HPO_4$, $Na_2SO_4$ and ions of the trace elements selenium, and zinc. Optionally, additional inorganic salt ingredients may include a manganese salt (e.g., $MnCl_2$), silicon, molybdenum, vanadium, nickel, and tin.

These trace elements may be provided in a variety of forms, preferably in the form of salts such as $Na_2SeO_3$, and ZnSO (or $Na_2SiO_3$, $(NH_4)_6Mo_7O_{24}$, $NH_4VO_3$, $NiSO_4$, SnCl for optional salts). These inorganic salts and trace elements may be obtained commercially, for example from Sigma (Saint Louis, Mo.).

Vitamin ingredients which may be included in the media of the present invention include biotin, choline chloride, D-$Ca^{++}$-pantothenate, folic acid, i-inositol, niacinamide, pyridoxine, riboflavin, thiamine and vitamins A and B12. These vitamins may be obtained commercially, for example from Sigma (Saint Louis, Mo.).

Protein synthesis procursors include amino acid ingredients. In one embodiment, the amino acid ingredients which may be included in the media of the present invention include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. These amino acids may be obtained commercially, for example from Sigma (Saint Louis, Mo.).

Alternatively, in some other embodiments, only essential amino acids are included in the media of the present invention. Certain cells, such as human cells must have adequate amounts of 9 amino acids to survive. These so called "essential" amino acids cannot be synthesized from other precursors. However, cysteine can partially meet the need for methionine (they both contain sulfur), and tyrosine can partially substitute for phenylalanine Such essential amino acids include: Histidine, Isoleucine, Leucine, Lysine, Methionine (and/or cysteine), Phenylalanine (and/or tyrosine), Threonine, Tryptophan, and Valine. In certain embodiments, only Histidine, Isoleucine, Leucine, Lysine, Threonine, Tryptophan, and Valine are included.

Some or all of the above ingredients, when admixed together in solution, can form a "basal medium." To this basal medium, other components, such as at least one nucleotide synthesis and/or salvage pathway precursors (e.g. hypoxanthine), epidermal growth factor (EGF), at least one agent increasing intracellular cyclic adenosine monophosphate (cAMP) levels, and at least one antioxidants, are added to formulate the complete culture media of the present invention. These latter added components, such as EGF and the cAMP-increasing agent(s) may be added to freshly formulated basal medium, or they may be admixed as in a stock solution stored frozen, preferably at about $-20°$ C. to about $-70°$ C., until being added to basal medium to formulate the complete medium of the present invention. This complete medium does not depend on BPE or other organ/gland extracts in animal cell culture media to achieved the desired cell growth/proloferation. The admixture may also be prepared as a 1-1000×formulation, most preferably as a 1×, 100×, 500× or 1000×formulation, which is then diluted appropriately into culture medium to provide a 1×final formulation in the complete media of the present invention.

The medium of the invention may also include one or more hormones, such as: progesterone, testosterone, hydrocortisone, and estrogen, and one or more growth factors such as: insulin and EGF (epidermal growth factor).

For example, the medium of the invention may comprise EGF, which may be natural or recombinant, and may be human or rodent. EGF available commercially (e.g., from GIBCO/LTI, Gaithersburg, Md.), isolated from natural sources or produced by recombinant DNA techniques (U.S. Pat. No. 4,743,679) according to methodologies that are routine in the art. To formulate the medium of the present invention, EGF should be added to the basal medium shown in Table II at a concentration of about 0.00001-10 mg/L, preferably about 0.0005-1 mg/L.

The medium of the invention may also include nucleotide analogs or precursors, such as hypoxanthine, xanthine, adenine, guanine, and thymidine that can be used in the salvage pathway synthesis of nucleotides.

The medium of the invention may also include lipid synthesis precursors, such as: cholesterol, linoleic acid, lipoic acid, or o-phosphoryl ethanolamine.

The medium of the invention also includes one or more cAMP agonists or agents that increase intracellular cAMP levels. A variety of such agents may be used in formulating the media of the present invention. Included are agents which induce a direct increase in intracellular cAMP levels (e.g., dibutyryl cAMP), agents which cause an increase in intracellular cAMP levels by an interaction with a cellular G-protein (e.g., cholera toxin and forskolin), agents which cause an increase in intracellular cAMP levels by acting as agonists of β-adrenergic receptors (e.g., isoproterenol) and agents which cause an increase in intracellular cAMP levels by inhibiting the activities of cAMP phosphodiesterases (e.g., isobutylmethylxanthine (IBMX) and theophylline). Most preferable for use in formulating the media of the present invention is cholera toxin. These cAMP-increasing agents are available commercially, e.g. from Sigma (St. Louis, Mo.), and are used at concentrations approximating those described in Green (Proc. Natl. Acad. Sci. USA 15:801-811 (1978)). For example, cholera toxin is added to the basal medium described above at a concentration of about 0-0.01 mg/L, preferably about 0-0.001 mg/L, and most preferably about 0-0.0001 mg/L. Dibutyryl cAMP, IBM, isoproterenol etc. can be added to achieve the same level of cAMP as cholera toxin.

It is also desirable to increase intracellular cAMP level by using agents such as cholera toxin, forskolin, G protein-coupled receptor agonists, PKC agonists. In addition, cells may have increased cAMP in response to the beta-adrenergic agonist isoproterenol (Iso), prostaglandin E(2) (PGE(2)), certain prostanoid receptor-selective agonists (beraprost, butaprost), and an adenosine receptor agonist. In addition, overexpression of AC type 6 or agents inhibiting cyclic nucleotide phosphodiesterases increased cellular cAMP levels.

The subject medium may also comprise one or more carbohydrate synthesis and energy metabolism precursors, such as D-glucose, sodium pyruvate, etc.

The subject medium may also comprise one or more carrier proteins, such as bovine serum albumin (BSA). Carrier protein may be a protein which transports specific substances through the cell membrane in which it is embedded and into the cell. Different carrier proteins may be required to transport different substances, as each one is designed to recognize only one substance, or group of similar substances. Certain carrier proteins may bind to one or more media components (such as growth factors, etc.) and confer them extra stability in the media, or to facilitate certain biological processes (e.g. acyl-carrier protein, sterol carrier protein, hormone carrier protein, etc.).

The subject medium may also comprise one or more carrier proteins, such as nonionic surfactants Tween 60 or Tween 80. Again, without wishing to be bound by any particular theory, such detergent components may help to wet, solubilize, emulsify, or disperse certain media components. For example, they may prevent aggregation of proteins such as BSA, increase solubility of certain components, and may even enhance the function of certain enzymes.

Although not considered essential, the subject medium may additionally comprise one or more buffer systems, such as HEPES and sodium bicarbonate buffer systems, such that a balanced pH is maintained in long-term culture. Frequent, constant or continuous change of culture medium may also help to restore medium pH in fast growing cells.

To illustrate, Table II below shows the composition of a medium formulation of the instant invention that supports long-term undifferentiated growth and proliferation of primary breast epithelial cells for at least about 4 weeks or at least about 15 population doubling (PD) in vitro, without any detectable genetic alterations, or losing differentiation potential. Primary mammalian epithelial cells can grow in such a medium for at least 4 weeks (or 15 population doublings), and up to several months, without any detectable genetic alterations, or losing differentiation potential.

In contrast, on average, cells isolated from similar tissues, when growing in other media, including the only commercially available medium MEGM® from Clonetics® (Cambrex Corp., East Rutherford, N.J.) at best support 4 weeks or less than 15 population doublings in vitro. Although a minor population of cell clones eventually escape (about $1 \times 10^{-5}$), such clones appear to have lost p16 activity, and may have additional genetic alterations that enable their escape from senescence.

In one embodiment, the subject medium does not support the growth or proliferation of fibroblasts and stromal cells. In fact, the subject medium may select against the growth or proliferation of these cells, possibly because of the absence of serum or tissue extracts in the subject medium formulation. Thus, the percentage of fibroblasts and other stromal cells decreases sharply after a few passages and population doublings, to the extent that no appreciable amount of fibroblast and stromal cell differentiation markers (e.g. vimentin) can be detected.

For example, the epithelial differentiation markers may include keratin 8, keratin 10, keratin 14, keratin 18, keratin 19, E-cadherin, p63, SMA (smooth muscle actin), and β-catenin.

Ex vivo tissue culture exposes cells to oxidative damage, metabolic stress and DNA damage that induce p53 and p16 genes, which in turn induce cell-cycle arrest, senescence and/or apotosis limiting the life-span cultured cells. In another embodiment, the media of the invention supports long-term stress-free growth and proliferation of primary cells. One indication of such stress-free growth in the subject medium is indicated by the low/undetectable expression level of CDK inhibitor p16 and tumor suppressor p53. These two proteins are typically induced to express at a high level in stressed cells, but not healthy growing cells in tissue culture media. In this embodiment the cells can be grown at 37° C., 5% $CO_2$ and varying $O_2$ concentrations, 1%, 3% or ambient air.

In another embodiment, the media of the invention is substantially free of at least one member selected from the group consisting of: serum, heparin, fibroblast growth factor (FGF), and bovine pituatary extract (BPE). In certain embodiments, none of the above listed components are present in the subject medium.

However, to the extent that such components do not substantially affect the performance of the medium in terms of supporting undifferentiated primary cell growth and proliferation, the subject medium may in certain embodiments include and tolerate the presence of one or more of such components.

Table I below is an example of a medium formula that can be used for short-term transport and/or storage of isolated primary cells, and may support undifferentiated growth of such cells to a lesser extent. The medium contains fewer components, which is easier and less expensive to make. Such medium can also be made by mixing about 50% Medium 199 (M199) and about 50% F12 (Ham) medium, and supplementing with glutamine, EGF, transferrin, insulin, 17B-estrodiol, o-phosphorylethanolamine, selenious acid, lionleic acid, BSA, triiodothyronine, hydrocortizone, cholera toxin, and HEPES, to approximately their corresponding concentrations listed in Table I.

It should be understood that the medium of the invention as listed in Tables I and II are merely for illustrative purposes only. Although the medium itself is sufficient for certain intended purposes, especially culturing primary mammary epithelial cells, not all components listed in these Tables may be necessary or even optimum for their intended purposes. A skilled artisan, partly depending on the need for the specific primary cells in question, could readily determine if any listed component is necessary and/or optimum by, for example, eliminating one component or changing the concentration of one component at a time and comparing the growth/proliferation of specific type of cultured cells in such a modified medium with the original medium. One or more components may also be substituted by other chemicals of similar properties when necessary. Such modified medium without one or more non-essential/unnecessary components are within the scope of the invention.

Similarly, a skilled artisan could also determine the optimal level of any given component for a particular cell type, by, for example, testing a range of concentrations (e.g., 10%, 25%, 50%, 75%, 100%, 2-, 5-, 10-, 20-, 50-, 100-, 200-, 500-, 1000-fold higher, or 10%, 25%, 50%, 75%, 100%, 2-, 5-, 10-, 20-, 50-, 100-, 200-, 500-, 1000-fold lower) for each listed component based on or starting from the listed concentration of that particular component. Some components have a listed range of concentrations. The proper or optimal concentration for any particular cell types can also be determined similarly starting from the listed concentration. In doing such tests, initial broad-range concentration tests may be narrowed down later based on the outcomes of the initial experiments. For example, for an initial test, the concentration of one component of interest may be changed to $10^{-3}$, $10^{-2}$, $10^{-1}$, 10-fold, 100-fold, and 1000-fold of the concentration listed in Table I. If the $10^{-2}$ test still supports the desired growth, while $10^{-3}$ fails to, then the 10-fold concentration difference between $10^{-2}$ and $10^{-3}$ may be further explored in the second round of test to pin-point the best ranges. Thus, media so optimized for specific cell types are also within the scope of the instant invention.

As will be readily apparent to one of ordinary skill in the art, the concentration of a given ingredient can be increased or decreased beyond the range disclosed and the effect of the increased or decreased concentration can be determined using only routine experimentation. The optimization of the present media formulations for any specific cell type can be carried out using approaches described by Ham (Ham, *Methods for Preparation of Media, Supplements and Substrata for Serum-Free Animal Culture*, Alan R. Liss, Inc., New York, pp. 3-21, 1984) and Waymouth (Waymouth, C., *Methods for Preparation of Media, Supplements and Substrata for Serum-Free Animal Culture*, Alan R. Liss, Inc., New York, pp. 23-68, 1984). The optimal final concentrations for medium ingredients are typically identified either by empirical studies, in single component titration studies, or by interpretation of historical and current scientific literature. In single component titration studies, using animal cells, the concentration of a single medium component is varied while all other constituents and variables are kept constant and the effect of the single component on viability, growth or continued health of the animal cells is measured.

The medium ingredients can be dissolved in a liquid carrier or maintained in dry form. If dissolved in a liquid carrier at the preferred concentrations shown above (i.e., a "1×formulation"), the pH of the medium should be adjusted to about 7.0-7.6, preferably about 7.1-7.5, and most preferably about 7.2-7.4. The osmolarity of the medium should also be adjusted to about 275-350 mOsm, preferably about 285-325 mOsm, and most preferably about 280-310 mOsm. The type of liquid carrier and the method used to dissolve the ingredients into solution vary and can be determined by one of ordinary skill in the art with no more than routine experimentation. Typically, the medium ingredients can be added in any order.

A cell culture medium is composed of a number of ingredients and these ingredients vary from one culture medium to another. A "1×formulation" is meant to refer to any aqueous solution that contains some or all ingredients found in a cell culture medium at working concentrations. The "1×formulation" can refer to, for example, the cell culture medium or to any subgroup of ingredients for that medium. The concentration of an ingredient in a 1×solution is about the same as the concentration of that ingredient found in a cell culture formulation used for maintaining or cultivating cells in vitro. A cell culture medium used for the in vitro cultivation of cells is a 1×formulation by definition. When a number of ingredients are present, each ingredient in a 1×formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic aced. A "1×formulation" of these amino acids contains about the same concentrations of these ingredients in solution. Thus, when referring to a "1×formulation," it is intended that each ingredient in solution has the same or about the same concentration as that found in the cell culture medium being described. The concentrations of ingredients in a 1×formulation of cell culture medium are well known to those of ordinary skill in the art. See Methods For Preparation of Media, Supplements and Substrate For Serum-Free Animal Cell Culture Allen R. Liss, N.Y. (1984), which is incorporated by reference herein in its entirety. The osmolarity and/or pH, however, may differ in a 1×formulation compared to the culture medium, particularly when fewer ingredients are contained in the 1×formulation.

A "10×formulation" is meant to refer to a solution wherein each ingredient in that solution is about 10 times more concentrated than the same ingredient in the cell culture medium. For example, a 10×formulation of RPMI-1640 culture medium may contain, among other ingredients, 2.0 g/L L-arginine, 0.5 g/L L-asparagine, and 0.2 g/L L-aspartic acid (compare 1×formulation, above). A "10×formulation" may contain a number of additional ingredients at a concentration about 10 times that found in the 1×culture medium. As will be readily apparent, "25×formulation," "50×formulation," "100×formulation," "500×formulation," and "1000×formulation" designate solutions that contain ingredients at about 25-, 50-, 100-, 500-, or 1000-fold concentrations, respectively, as compared to a 1×cell culture medium. Again, the osmolarity and pH of the media formulation and concentrated solution may vary.

Preferably, the solutions comprising ingredients are more concentrated than the concentration of the same ingredients in a 1×media formulation. The ingredients can be 10-fold more concentrated (10×formulation), 25-fold more concentrated (25×formulation), 50-fold more concentrated (50×concentration), or 100-fold more concentrated (100×formulation). More highly concentrated formulations can be made, provided that the ingredients remain soluble and stable. See U.S. Pat. No. 5,474,931 (entire contents incorporated herein by reference), which is directed to methods of solubilizing culture media components at high concentrations.

If the media ingredients are prepared as separate concentrated solutions, an appropriate (sufficient) amount of each concentrate is combined with a diluent to produce a 1×medium formulation. Typically, the diluent used is water but other solutions including aqueous buffers, aqueous saline solution, or other aqueous solutions may be used according to the invention.

The culture media of the present invention are typically sterilized to prevent unwanted contamination. Sterilization may be accomplished, for example, by filtration through a low protein-binding membrane filter of about 0.1-1.0 μm pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1×sterile medium formulation. Autoclaving or other elevated temperature-based methods of sterilization are not favored, since many of the components of the present culture media are heat labile and will be irreversibly degraded by temperatures such as those achieved during most heat sterilization methods.

As will be readily apparent to one of ordinary skill in the art, each of the components of the culture medium may react with one or more other components in the solution. Thus, the present invention encompasses the formulations disclosed in Tables I and II, supplemented as described above, as well as any reaction mixture which forms after these ingredients are combined.

Many tissue culture media typically contain one or more antibiotics, which are not necessary for cell growth/proliferation per se, but are present to inhibit the growth of other undesirable microbes, such as bacteria and/or fungi.

Antibiotics are natural chemical substances of relatively low molecular weight produced by various species of microorganisms, such as bacteria (including *Bacillus* species), actinomycetes (including *Streptomyces*) and fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are: (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

Thus for convenience and other practical reasons, the subject media may be additionally supplemented by one or more antibiotics or other substances that inhibit the growth/proliferation of undesirable bacteria/fungi/virus. In other embodiments, however, the subject medium may be free of any antibiotics to ensure optimum growth of primary cells. Extra care should be taken when handling cells growing in antibiotic-free medium in order to avoid possible contamination.

TABLE I

Secondary Culture Medium without Optional Components

| Components | Concentration (mg/L)* |
|---|---|
| 2-deoxy-D-ribose | 0.25 |
| Adenine sulfate | 5 |
| Adenosine 5'-phosphate | 0.1 |
| Adenosine 5'-triphosphate | 0.5 |
| Ascorbic acid | 0.025 |
| Biotin | 0.00865 |
| Bovine serum albumin (BSA) | 900-1250 |
| Calcium chloride (anhydrous) | 16.61 |
| Calcium chloride ($CaCl_2$) | 100 |
| Cholera toxin | 0-0.0001 |
| Choline chloride | 7.25 |
| Cupric sulfate ($CuSO_4 \cdot 5H_2O$) | 0.00125 |
| D-Calcium pantothenate | 0.255 |
| D-Glucose | 1000-4000 |
| Epidermal Growth Factor (EGF) | 0.0005-1.0 |
| Ferric nitrate ($Fe(NO_3)_2 \cdot 9H_2O$) | 0.35 |
| Ferric sulfate ($FeSO_4 \cdot 7H_2O$) | 0.417 |
| Folic Acid | 0.655 |
| Glycine | 28.75 |
| Guanine hydrochloride | 0.15 |
| Hypoxanthine Na | 2.585-13.6 |
| i-Inositol | 9.025 |
| Insulin | 10-15 |
| L-Alanine | 16.95 |
| L-Arginine hydrochloride | 140.5 |
| L-Asparagine•$H_2O$ | 7.505 |
| L-Aspartic Acid | 21.65 |
| L-Cysteine-HCl•$H_2O$ | 17.61 |
| L-Cystine-2HCl | 13 |
| L-Glutamic Acid | 44.85 |
| L-Glutamine | 269 |
| L-Histidine-HCl•$H_2O$ | 21.44 |
| L-Hydroxyproline | 5 |
| Linoleic Acid | 5.39 |
| Lipoic Acid | 0.105 |
| L-Isoleucine | 22 |
| L-Leucine | 36.55 |
| L-Lysine hydrochloride | 53.25 |
| L-Methionine | 9.75 |
| L-Phenylalanine | 15 |
| L-Proline | 37.25 |
| L-Serine | 17.75 |
| L-Threonine | 20.95 |
| L-Tryptophan | 6.02 |
| L-Tyrosine 2Na•$2H_2O$ | 23.9 |

TABLE I-continued

Secondary Culture Medium without Optional Components

| Components | Concentration (mg/L)* |
|---|---|
| L-Valine | 18.35 |
| Magnesium Chloride (anhydrous) | 28.61 |
| Magnesium sulfate ($MgSO_4$) | 48.835 |
| Niacin | 0.0125 |
| Niacinamide | 0.0305 |
| Para-aminobenzoic acid | 0.025 |
| Potassium chloride (KCl) | 311.8 |
| Putrescine-2HCl | 0.0805 |
| Pyridoxal hydrochloride | 0.0125 |
| Pyridoxine hydrochloride | 0.0425 |
| Riboflavin | 0.0235 |
| Ribose | 0.25 |
| Selenous acid | 0.0078 |
| Sodium acetate | 25 |
| Sodium bicarbonate ($NaHCO_3$) | 1688 |
| Sodium chloride (NaCl) | 7199.5 |
| Sodium phosphate ($NaH_2PO_4 \cdot H_2O$) | 70 |
| Sodium phosphate, dibas (anhydrous) | 71 |
| Thiamine hydrochloride | 0.155 |
| Thymidine | 0.35 |
| Thymine | 0.15 |
| Transferrin | 11.25 |
| Uracil | 0.15 |
| Zinc sulfate ($ZnSO_4 \cdot 7H_2O$) | 0.431 |

*concentrations are expressed as units/total volume.

Note:

the concentrations listed above are not absolute and invariable. Since different cell types may have different growth needs, it is contemplated that generally, a 2-10 fold variation (increase or decrease) for each value is an acceptable range of concentration (supra). Some components may tolerate an even larger variation of final concentration (See Example below). Further optimization can be achieved using these starting concentrations (see above). One of the media prepared according to Table I is named "WIT medium" in Example IV below. Such a medium typically does not need to contain cholera toxin or other agents that increase intracellular cAMP levels, and is suitable for primary cells transformed (immortalized) by telomerase catalytic subunits.

TABLE II

Primary Culture Medium with Optional Components

| Components | Concentration (mg/L*) |
|---|---|
| *17-beta-estradiol | 0.00034-0.0034 |
| 2-deoxy-D-ribose | 0.25 |
| Adenine sulfate | 5 |
| Adenosine 5'-phosphate | 0.1 |
| Adenosine 5'-triphosphate | 0.5 |
| *Alpha-tocopherol acetate | 0-2 |
| *Alpha-tocopherol phosphate | 0.005 |
| Ascorbic acid | 0.025 |
| Biotin | 0.00865 |
| Bovine serum albumin (BSA) | 1250-9000 |
| *Calciferol (Vitamin D2) | 0.05 |
| Calcium chloride (anhydrous) | 2-16.61 |
| Calcium chloride ($CaCl_2$) | 5-100 |
| Cholera toxin | 0-0.1 |
| *Cholesterol | 0.1-2.2 |
| Choline chloride | 7.25 |
| Cupric sulfate ($CuSO_4 \cdot 5H_2O$) | 0.00125 |
| D-Calcium pantothenate | 0.255 |
| D-Glucose | 1000-2000 |
| Epidermal Growth Factor (EGF) | 0.0005-0.01 |
| Ferric nitrate ($Fe(NO_3)_2 \cdot 9H_2O$) | 0.35 |
| Ferric sulfate ($FeSO_4 \cdot 7H_2O$) | 0.417 |
| Folic Acid | 0.655 |
| *Glutathione (reduced) | 0.025-1.0 |
| Glycine | 28.75 |
| Guanine hydrochloride | 0.15 |
| *HEPES pH 7.5 | 10 mM |
| *Hydrocortisone | 0.00043-0.5 |
| Hypoxanthine Na | 2.585-13.6 |
| i-Inositol | 9.025 |
| Insulin | 10-20 |
| L-Alanine | 16.95 |
| L-Arginine hydrochloride | 140.5 |
| L-Asparagine•$H_2O$ | 7.505 |

TABLE II-continued

Primary Culture Medium with Optional Components

| Components | Concentration (mg/L*) |
| --- | --- |
| L-Aspartic Acid | 21.65 |
| L-Cysteine-HCl•H$_2$O | 17.61 |
| L-Cystine-2HCl | 13 |
| L-Glutamic Acid | 44.85 |
| L-Glutamine | 269 |
| L-Histidine-HCl•H$_2$O | 21.44 |
| L-Hydroxyproline | 5 |
| Linoleic Acid | 5.39 |
| Lipoic Acid | 0.105 |
| L-Isoleucine | 22 |
| L-Leucine | 36.55 |
| L-Lysine hydrochloride | 53.25 |
| L-Methionine | 9.75 |
| L-Phenylalanine | 15 |
| L-Proline | 37.25 |
| L-Serine | 17.75 |
| L-Threonine | 20.95 |
| L-Tryptophan | 6.02 |
| L-Tyrosine 2Na•2H$_2$O | 23.9 |
| L-Valine | 18.35 |
| Magnesium Chloride (anhydrous) | 28.61 |
| Magnesium sulfate (MgSO$_4$) | 48.835 |
| *Menadione (Vitamin K3) | 0.005 |
| Niacin | 0.0125 |
| Niacinamide | 0.0305 |
| *o-phosphoryl ethanolamine | 5.65 |
| Para-aminobenzoic acid | 0.025 |
| *Phenol red | 10.6 |
| Potassium chloride (KCl) | 311.8 |
| *Progesterone | 0.0004 |
| Putrescine-2HCl | 0.0805 |
| Pyridoxal hydrochloride | 0.0125 |
| Pyridoxine hydrochloride | 0.0425 |
| Riboflavin | 0.0235 |
| Ribose | 0.25 |
| Selenous acid | 0.0078 |
| Sodium acetate | 25 |
| Sodium bicarbonate (NaHCO$_3$) | 1688 |
| Sodium chloride (NaCl) | 7199.5 |
| Sodium phosphate (NaH$_2$PO$_4$•H$_2$O) | 70 |
| Sodium phosphate, dibas (anhydrous) | 71 |
| *Sodium pyruvate | 55 |
| *Testosterone | 0.00036 |
| Thiamine hydrochloride | 0.155 |
| *Thriiodothyronine | $0\text{-}0.168 \times 10^{-6}$ |
| Thymidine | 0.35 |
| Thymine | 0.15 |
| Transferrin | 11.25 |
| *Tween 80 | 10 |
| Uracil | 0.15 |
| *Vitamine A (acetate) | 0.05 |
| *Vitamine B12 | 0.7 |
| *Xanthine-Na | 0.17 |
| Zinc sulfate (ZnSO$_4$•7H$_2$O) | 0.431 |

*concentrations are expressed as units/total volume.

Note:
components with asterisks (*) are optional components. All optional components do not need to be present in the final medium at least for short term - as few as 1 to a maximum of 19 optional components might be present in the final medium. Preferred medium contains all 19 optional components.

The medium of the instant invention can be made from individual components separately purchased from various chemical venders. Alternatively, certain commercial medium may be conveniently mixed and supplemented by additional components for make the subject medium. For example, in one embodiment, the subject medium may comprise about 50% Medium 199 (M199) and about 50% F12 (Ham) medium, supplemented with glutamine, EGF, transferrin, insulin, progesterone, testosterone, 17B-estrodiol, o-phosphorylethanolamine, selenious acid, lionleic acid, BSA, triiodothyronine, hydrocortizone, cholera toxin, HEPES, and other components to approximately their corresponding concentrations as listed in Table II.

The medium of the instant invention may be liquid or solid powder, or a combination of both. The liquid form may be a complete medium, which contains all the components sufficient to support the growth/proliferation of the target cells. Alternatively, the liquid media may be stored as separate packages, such that each individual package may be stored at its appropriate conditions (temperature, humidity, etc.). For example, most of the components listed in the table, if desired to be in a medium of the instant invention, can be pre-dissolved in a single solution and stored at appropriate conditions (e.g. 4° C. in a dark and dry place, etc.). Other components, which could be unstable at the storage conditions for the other components, or which could react slowly with other components, or which is otherwise better kept as a separate stock, may be stored under a different set of conditions (e.g. −20° C. or −80° C., etc.). It is only shortly or immediately before use are these separately stored components brought together to constitute the whole medium. Each separate packages may be marketed or sold separately, or as different concentrated stocks (e.g. 2×, 5×, 10×, 100×, 1000×, etc.).

Similarly, the complete medium or individual components, packages thereof could be in the form of dry powder, which, upon reconstitution with an aqueous solution (such as water), will yield the desired medium, or its concentrated stocks (2×5×, or 10×, etc.).

Components that can be, or better kept as separate stocks just prior to use include: growth factors (e.g. Epidermal Growth Factor), hormones (e.g. progesterone, testosterone), other unstable enzymes/proteins (e.g. transferrin, insulin, cholera toxin, etc.), steroids (e.g. hydrocortisone, cholesterol), vitamins (Vitamins A, B$_{12}$, K$_3$), pH indicators (e.g. phenol red), one or more buffer components (e.g. sodium biocarbonate, HEPES) and other chemicals (e.g. glutathione, 17-β-estradiol, o-phosphoryl ethanolamide, etc.).

In certain embodiments, at least some or all components of the medium is in liquid/aqueous form. In other embodiments, at least some or all components of the medium is in solid/powder form.

The media of the invention are suitable for a variety of primary glandular epithelial cells, including epithelial cells from breast (luminal), prostate, lung, GI tract (e.g. salivary gland, small and large intestine, colon, stomach, pancreas, liver, gall bladder, etc.), cervix, endometrium/uterus, and ovary. The media may also be suitable for culturing primary endothelial cells.

In addition, the subject medium is also suitable to support long-term growth, proliferation, and/or differentiation of primary breast epithelial cells induced to express: (1) telomerase catalytic subunit, (2) a first polypeptide functions in the same signaling pathway(s) as does the SV40 large T antigen (such as SV40 Large T antigen), and (3) a second polypeptide functions in the same signaling pathway as does the mutant H-ras oncogene product (such as H-Ras), for at least about 15 weeks or at least about 35 population doubling (PD) in vitro, without losing tumorigenicity.

The media of the invention are suitable for a variety of primary glandular epithelial cells from different mammals, including human and other non-human mammals. The latter further includes: non-human primates (e.g. monkey, guerilla, etc.), mouse, rat, rabbit, domestic cattle, horse, pig, sheep, goat, dog, and cat.

In certain embodiments, the medium supports the growth, proliferation, and/or differentiation of cells from normal glandular epithelial cells of an organ/tissue selected from: breast, prostate, ovary, pancreas, stomach, intestine, colon, endocervix, kidney, skin, lung, uterus, parotid gland, or fallopian tube.

In certain embodiments, the medium supports the growth, proliferation, and/or differentiation of endometrial cells or cervical cells.

In certain embodiments, the medium supports the differentiation of breast glandular epithelial cells to luminal phenotype, but not basoid phenotype. Such luminal phenotype is characterized by specific keratin expression profiles typical of luminal mammary epithelial cells.

In certain embodiments, the subject medium supports undifferentiated growth and proliferation of a population of breast progenitor cells characterized by expression of CD44, CD24 and ESA (epithelial cell surface antigen) in at least about 85% of the cells, or at least about 88%, 90%, 95% 99% or near 100% of the cells.

Another aspect of the invention relates to a composition of matter comprising a mixture of solid form chemicals, the chemicals, when dissolved in a given volume of an aqueous solvent, becomes the medium of any one of the above described media.

IV. Isolation and Culturing of Primary Cells

Another aspect of the invention relates to the use of the subject medium for isolating primary cells, such as primary mammalian glandular epithelial cells substantially free of other cell types, including stromal cells and myoepithelial cells.

In one embodiment, the method comprise: (1) providing tissues containing the primary cells from the mammal; (2) separating or enriching the primary cells from other cells in the tissues; (3) plating the primary cells separated/enriched in (2) on a tissue culture container with mixed (+/−) charge surface, in the subject medium for about a week, with frequent (e.g. daily) medium change; (4) (optionally) removing residual cells other than the primary cells by selective trypsin digestion using low concentration of trypsin at about 0.025%, over a period of 1-3 days; (5) harvesting the primary cells by using high concentration of trypsin at about 0.15%, and transferring the harvested the primary cells to a new tissue culture container with mixed (+/−) charge surface in the subject medium, thereby isolating the primary cells from the mammal.

Although not limiting, the method of the invention is particularly suitable to isolate primary glandular epithelial cells, such as mammary glandular epithelial cells. Other primary cell sources include such tissues as: breast, prostate, ovary, pancreas, stomach, intestine, colon, endocervix, kidney, skin, lung, uterus, parotid gland, or fallopian tube.

"Substantially free" as used herein refers to at least about 80% pure, preferably 85%, 90%, 95%, 99% or more pure population of the desired cells in the whole cell population. The medium of the invention not only supports the long-term growth and proliferation of the desired mammalian glandular epithelial cells, but also suppresses the growth of other major competitor cell types, including stromal cells and myoepithelial cells. Therefore, after about 1-2 weeks of culturing and passaging of the primary cells isolated from minced tissue blocks, the glandular epithelial cells are selectively enriched, and eventually become the only actively proliferating cell types in tissue culture.

In one embodiment, a tissue with the desired glandular epithelial cells (such as breast, prostate, ovary, pancreas, stomach, intestine, colon, endocervix, kidney, skin, lung, uterus, Parotid gland, or fallopian tube, etc.) is obtained from a human or non-human patient, and minced down to chunks/cubes/fragments of about 1-2 mm in dimension. Cells in the fragments are then separated by, for example, overnight collagenase digestion in suitable buffer and temperature (e.g. Hank's buffered saline solution at 37° C. overnight). Other methods, such as mechanical means (passing the minced tissue through a steel mesh using a plunger, optionally followed by a cotton wool column, etc.) may also be used.

Glandular epithelial cells tend to form clumps of organoids. Low speed centrifugations at about 50-300 g could be used to separate these organoids from other single cells, which are mostly stromal cells and myoepithelial cells. The isolated primary cells and organoids are then plated on a tissue culture container surface that has mixed (+/−) charge surface.

Most traditional tissue culture cell container surfaces are negatively charged (see the numerous —COOH groups below, which, at neutral pH, tend to slightly dissociated and assume a negative (anionic) charge). This leads to poor attachment of the desired primary cells to the container surfaces, and thus preferably should not be used. Suitable tissue culture container with mixed charges include both positive (see the —NH$_2$ groups, which may protonate and assume a positive charge (cationic) at neutral pH) and negative charges (see the —COOH groups and above). BD Primaria™ Cultureware (BD Biosciences) manufactures such mixed-charge tissue culture containers.

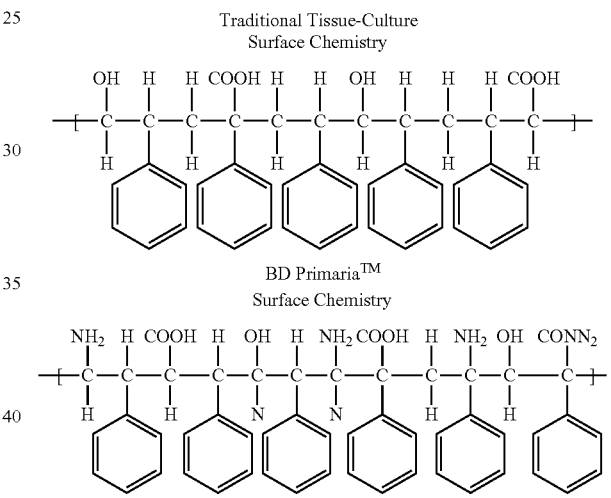

An alternative method is to coat the tissue culture surface with BD Matrigel™ matrix (BD Biosciences)—a solubilized basement membrane preparation extracted from EHS mouse sarcoma, a tumor rich in ECM proteins. Its major component is laminin, followed by collagen IV, heparan sulfate proteoglycans, and entactin. Other Matrigel™ equivalents may also be used.

After 7-10 days of culturing on suitable surfaces, with daily change of medium, cells can be harvested by first treating the container with a low concentration of trypsin (e.g. 0.025%) to remove loosely attached cells (mostly stromal cells), followed by a treatment using higher concentration of trypsin (e.g. 0.075%). If desired, such passage can be repeated more than once to significantly enrich for the desired primary glandular cell population. Once the enrichment step is completed, cells can be grown in secondary medium for all future culturing.

Another aspect of the invention relates to a method of subculturing primary cells, such as primary glandular epithelial cells growing in the subject media, comprising trypsinizing the attached cells with 0.075% trypsin, and harvesting cells in primary medium supplemented with trypsin inhibitor(s) such as 5% calf serum or equivalent serum. This is helpful partly because the serum-free formula of the subject medium does not contain any of the natural trypsin inhibitors in various serum preparations in other media, thus cells growing in the subject media are potentially more sensitive to the presence of trace amount of active trypsin, which may prevent effective attachment of the cells to tissue culture surfaces. As soon as the cells attach to a suitable tissue culture container, such as the BD Primaria™ containers, the serum-supplemented medium is changed back to the medium of the instant invention.

Another aspect of the invention relates to a method of subculturing primary cells, such as primary glandular epithelial cells growing in the subject media, comprising trypsinizing the attached cells with 0.15% trypsin, and harvesting cells in primary medium supplemented with trypsin inhibitor(s) such as 5% calf serum or equivalent serum. This is helpful partly because the serum-free formula of the subject medium does not contain any of the natural trypsin inhibitors in various serum preparations in other media, thus cells growing in the subject media are potentially more sensitive to the presence of trace amount of active trypsin, which may prevent effective attachment of the cells to tissue culture surfaces. As soon as the cells attach to a suitable tissue culture container, such as the BD Primaria™ containers, the serum-supplemented medium is changed back to the medium of the instant invention.

A related aspect of the invention provides a primary cell isolated using the subject media and methods, wherein the isolated primary cells grow and/or proliferate in the subject medium for at least about 4 weeks or at least about 15 population doubling (PD) in vitro, without any detectable genetic alterations, or losing differentiation potential.

In a preferred embodiment, the primary cell is a primary glandular epithelial cell, such as a primary breast/mammary epithelial cell. In other embodiments, the primary glandular epithelial cell is from a tissue/organ selected from: prostate, ovary, pancreas, stomach, intestine, colon, endocervix, kidney, skin, lung, uterus, Parotid gland, or fallopian tube.

The primary cells of the invention can proliferate in the subject media for at least about 5, 6, 7, 8, 9, 10, 11, 12, 13, 14, 15 or more weeks, or at least about 16, 20, 25, 30, 35 or more population doubling (PD) in vitro, without going into a state of senescence.

Similar primary cells, when growing in other media, such as the commercially available MEGM media, on average go into the state of senescence in about 3-4 weeks, or about 10-15 population doublings. A minor population (about $10^{-5}$) of such senesced cells might eventually escape and enter another phase of growth, but such escaped cells almost always contain additional mutations, such as p16 inactivation. In contrast, the isolated primary cells of the invention continue to grow in the subject media for much longer without incurring such mutations or entering a state of senescence.

In a related embodiment, the isolated primary cells are substantially free of stress gene (e.g. p16, p53) expression. "Substantially free" as used herein means at least about 90% free, preferably 95% free, 99% or more free as compared to that of the cells growing in other media, including the MEGM media.

In another embodiment, the isolated primary cells are substantially free of fibroblasts and stromal cells. "Substantially free" as used herein means at least about 90%, preferably 95%, 99% or more cells are the isolated primary cells (not fibroblasts or stromal cells). Alternatively, the expresssion level of fibroblast marker, such as vimentin, is less than 10%, preferably less than 5%, 1% or lower in the subject isolated primary cells as compared to that of primary cells growing in other media, including the MEGM media.

In another embodiment, the isolated primary cells of the invention are hormone responsive before and during culturing in the medium. For example, in the case of isolated primary mammary epithelial progenitor cells, the cells are responsive to estrogen, progesterone, and testosterone. Other isolated primary cells are responsive to hormones to which they respond before being isolated from the original tissue.

In a preferred embodiment, the primary mammalian glandular epithelial cells are isolated breast progenitor epithelial cells (BPEC) that can further differentiate into epithelial cells of luminal phenotype.

For example, the method may comprise: (1) isolating and culturing the mammary epithelial progenitor cells according to the subject method of the invention as described above; (2) inducing the differentiation of the mammary epithelial progenitor cells to epithelial cells of luminal phenotype. To illustrate, step (2) above may be effectuated by culturing cells in 3-D culture with EHS.

The differentiation may be characterized by expression of markers specific for luminal phenotype. Suitable markers may include one or more of: keratin 8, keratin 18, E-cadherin, and β-catenin.

To facilitate isolating and culturing of glandular epithelial cells from a mammal, the invention also provides a kit comprising a carrier means having in close confinement therein one or more container means: (1) wherein a first container means contains any of the subject medium described above; (2) an instruction for isolating and subculturing glandular epithelial cells from the mammal. The kit may further comprise collagenase and/or trypsin. The collagenase may be supplied in Hank's buffered saline solution (HBSS). The trypsin may be supplied in a high concentration of about 0.15% and a low concentration of about 0.025%.

The invention also provides a kit for isolating and culturing glandular epithelial cells from a mammal, the kit comprising a carrier means having in close confinement therein one or more container means: (1) wherein a plurality of the container means, each individually contains, in proportion, solid forms of the components for any of the subject medium described above, such as that listed in Table II; (2) an instruction for making these media; (3) an instruction for isolating and sub-culturing glandular epithelial cells from the mammal.

In some embodiments, at least some of the components are stored at different temperatures as that for other of the components.

In some embodiments, at least some of the components are stored as liquid.

In some embodiments, at least some of the components are stored as solid powder.

In another aspect, PCT application WO 00/73420A2 describes a method of immortalizing and transforming normal somatic cells, including human mammary epithelial cells (HMEC) to immortalized and tumorigenic cells, the teaching of WO 00/73420A2 can be applied here in the isolated primary glandular cells of the invention (including BPEC). The entire content of which is incorporated herein by reference.

V. Tumor Stem Cell-Like Cells

In addition to be suitable for culturing normal mammalian primary epithelial cells, the subject media is also suitable for culturing primary cell-derived, tumor stem cell-like cells. Thus, yet another aspect of the invention relates to isolating/ establishing/purifying model tumor stem cells, and using such model tumor stem cells for screening drugs specifically or preferentially targeting tumor stem cells.

The identification of a breast cancer stem cell represents a major step forward in the elucidation of the breast cancer tumor hierarchy and signals the beginning of a new era of breast cancer research. The most important outcome of these studies extend beyond the breast cancer field to cancer research in general. Although the cancer stem cell hypothesis is well established, much modern cancer research still treats tumors as homogeneous collections of cells that can be simply disrupted for biochemistry studies or for gene expression profiling. The focus of future studies in cell signaling, molecular and cellular comparisons of normal and tumorigenic pathways, gene expression profiling, and drug development must include the cancer stem cell. This in turn will require the use of primary tissue and not cell lines, functional transplantation assays for the cancer stem cell, and cell purification using cell surface or metabolic properties to isolate enriched populations.

In the breast cancer field, the BrCa-IC are key to understanding the origin and maintenance of breast cancer. With this knowledge, it is possible and desirable to design therapies targeted to the unique properties of the tumor stem cell to enable selective killing. Indeed, all of the rich information that has been gained on tumorigenic cellular pathways in cancer, including breast cancer, needs to be reevaluated in light of the functional heterogeneity that exists in the tumor clone. For example, the biological consequence of a particular signaling pathway might be different in the rare BrCa-IC compared with the more numerous non-BrCa-IC cells.

Despite the importance of cancer stem cell research, there has been no easy way of isolating and culturing cancer stem cells in vitro. In the study by Al-Hajj et al., human tumor tissues were cut up into about 2×2×2 mm cubes, and implanted directly into experimental animals. Although cell sorting using markers such as CD44 and CD24 helps to isolating/purifying such stem cells, a method of isolating or purifying such cancer stem cells to a relatively pure, homogeneous population, followed by further culturing in vitro has not been provided. In addition, partly due to the inherent characteristic of cancer such as genetic instability, the genetic composition of the tumor cells isolated based on CD44 and CD24 expression is heterogeneous and unstable.

Thus an aspect of the instant invention provides a relatively simple way to isolate, purify, enrich, and/or establish cancer stem cell-like cells derived from normal primary cells of the invention, including those derived from primary breast epithelial cells. As such it allows direct comparison of normal primary cells to tumorigenic and metastatic cancer stem cells that are directly derived from these normal cells. Such a direct comparison would not be possible for tumor stem cells that are isolated from patient samples, as the tumor initiating normal cells have been already transformed and no longer exist by definition. Moreover, high throughput drug and genetic screening requires in vitro culturing of such cells. While methods of purifying these cells are available, in vitro culture of them have not been possible. Therefore the instant invention described in this application has two advantages compared to existing technology, it provides matched normal controls for direct comparison to tumor stem cells, and it allows in vitro cultivation of both normal and tumor stem cells for drug and genetic screening.

To illustrate, normal breast tissue (or other tissues for other primary cells) obtained from a mammalian patient (e.g. human), preferably those freshly dissected from the patient (within 1-2 hours), are cut down in sterile medium (such as RPMI medium 1640) on ice to tissue fragments of 1-2 mm in size. Such tissue fragments are then digested for 3-4 hours to overnight at 37° C. with collagenase to yield a mixture of organoids and single cells (mostly stromal cells and epithelial cells). The mixture is then centrifuged 3 times, at about 20 g for 3 minutes each to enrich for the organoids, which are then plated in the subject primary media on mixed-charge tissue culture containers (e.g. Primaria™). The organoids are cultured for about 2-3 weeks, including 2-3 passages of cells to new culture containers to selectively eliminate stromal cells.

Using this method, breast epithelial progenitor cells were purified from normal breast tissues. Notably the resulting cells are largely $ESA^+$, $CD44^+$, $CD24^\pm$, similar to the breast cancer stem cells isolated from patients suggesting that this is a preexisting expression profile that was not a result of genetic events in the cancer cells, a conclusion that could not have been made by simply purifying tumor stem cells from patient samples.

Thus in one embodiment, the invention relates to a tumorigenic cell derived from a cultured mammalian primary epithelial cell isolated using the methods and media of the invention (e.g. BPEC, supra), the cell having stably incorporated therein and stably expressing exogenous DNA which, when expressed in such a cell, results in production of a tumorigenic cell that grows in an anchorage-independent manner and forms tumors in immuno-compromised animals (e.g. mice) into which the tumorigenic cell (BPLER) or its progeny are introduced. In a preferred embodiment, one or more tumors are generated in at least about 40-50% of injected animals in a xenograph transplant model, if a total of less than about 10,000, or less than about 5,000, or less than about 1,000, or less than about 500, or less than about 100 of such tumorigenic cells are injected into each animal.

Consistent with the findings of Al-Hajj at al. and similar to tumor stem cells isolated from human patient samples, the tumors that are generated as described above consist of a tumor stem cell fraction and their non-tumorigenic progeny. This was illustrated by isolating $CD24^+$ and $CD24^-$ cells from BPLER explants and re-injecting them into nude mice. As expected, the $CD24^-$ cells were tumorgenic and $CD24^+$ cells were not tumorigenic. The same phenomenon was also illustrated with cells from tissue culture; $CD44^{high}$ cells and $CD44^{low}$ cells were separated by FACS sorting and injected into nude mice and only the $CD44^{high}$ fraction was able to grow tumors.

In one embodiment, the exogenous DNA is incorporated into genomic DNA of the cultured primary glandular cell (e.g. BPEC). The exogenous DNA may comprises: (a) DNA that encodes a telomerase catalytic subunit; (b) DNA that encodes a first oncogene or suppressor/inhibitor of a tumor suppresor gene; and (c) DNA which encodes a second, distinct oncogene (or suppresor of a tumor suppresor gene), wherein the first oncogene (or the first TS gene inhibitor) and the second oncogene (or the second TS gene inhibitor) function in two different biochemical pathways in cells.

For example, the DNA of (a) may be a cDNA that encodes human telomerase catalytic subunit; the DNA of (b) may be a cDNA that encodes an oncogene which functions in a first biochemical pathway; while the DNA of (c) is a cDNA that encodes an oncogene which functions in a second biochemical pathway, wherein the first biochemical pathway and the second biochemical pathway are two distinct biochemical pathways.

In a preferred embodiment, the first biochemical pathway and the second biochemical pathway are signaling pathways and the cDNA of (b) encodes an oncogene that functions in the same signaling pathway as does the mutant H-ras oncogene product and the cDNA of (c) functions in the same signaling pathways as does the SV40 large T antigen-encoded oncoprotein, wherein the functional effects of the cDNA of (b) and the functional effects of the cDNA of (c) on their respective signaling pathways in the normal human somatic cell in which human telomerase catalytic subunit is ectopically expressed result in production of a tumorigenic epithelial cell. For example, the DNA of (b) may be a cDNA which encodes the mutant H-ras oncogene product and the DNA of (c) may be a cDNA which encodes the SV40 large T antigen oncogene product.

One type of DNA introduced into the normal cells in one embodiment of the method of the present invention is DNA encoding the telomerase catalytic subunit of a telomerase holoenzyme. The DNA can be genomic DNA or cDNA and can be from a wide variety of organisms in which it occurs naturally (e.g., human, mouse, pig, rat, dog, monkey), provided that, when it is expressed or functions in glandular epithelial cells, it produces a product which has substantially the same function as does (human) telomerase catalytic subunit. Alternatively, DNA encoding telomerase catalytic subunit can be produced using recombinant DNA methods or can be chemically synthesized. As used herein, the term "DNA encoding telomerase catalytic subunit" encompasses DNA obtained from or produced by any of these sources or methods. In one embodiment of the present invention, the DNA encodes the human telomerase catalytic subunit and, in a specific embodiment, is hTERT. (Nakamura and Cech, *Cell* 92: 587-590, 1998, Meyerson et al., *Cell* 90: 785-795, 1997). Alternatively, exogenous DNA that does not itself encode telomerase catalytic subunit, but activates or enhances expression of an endogenous gene encoding the subunit is introduced into normal human somatic cells, in which it activates a "silent" endogenous gene encoding the catalytic subunit or enhances expression of the endogenous gene encoding the catalytic subunit already being expressed in the cell.

The second type of DNA introduced into the normal cells in the present method is DNA comprising at least one oncogene. The oncogene can be any oncogene which, when expressed or functional in normal human somatic cells in which telomerase catalytic subunit is ectopically expressed, results in the production of the tumorigenic cells upon culturing/propagation of the recipient normal human cell. Preferably, the oncogene(s) introduced into normal human somatic cells is an oncogene(s) characteristics (causative) of malignant human tumors. As a result, the tumorigenic cells produced contain an oncogene(s) present in naturally occurring human malignant or cancerous tumors and are useful in methods described herein such as methods of assessing the ability of a candidate drug to inactivate or inhibit the oncogene(s) or render tumor cells more vulnerable to other drugs or forms of treatment, such as radiation or laser therapy.

As used herein, the term "DNA comprising an oncogene" encompasses DNA whose expression results in production of an oncoproduct, such as an oncoprotein, and DNA which itself functions as an oncogene, such as by inactivating a resident tumor suppressor gene or by activating a resident proto-oncogene. It encompasses DNA that comprises or encodes all of the types of oncogenes described herein. The oncogene can be, for example, H-ras and K-ras, her2-neu, RET, sis , (PDGF) N-myc, L-myc, c-myc, bcl-1, bcl-2, src, and its family of related genes, MDM2 and any oncogene found in human tumor cells. The oncogene can also be a viral oncogene, such as SV40 large T, polyoma middle T, human papillomavirus E6 and E7, and the Epstein-Barr virus, and hepatitis B virus and tumor suppressor genes such as: APC, DPC4, NF-1, NF-2, p53, RB, MTS1, WT1, BRCA1, BRCA2, VHL, and PTEN. Entire oncogenes or portions thereof sufficient to result in the production of tumorigenic cells can be used. One oncogene or a combination of two or more oncogenes, such as a combination of two or more of the oncogenes listed, can be co-expressed with ectopically expressed telomerase catalytic subunit to produce tumorigenic cells.

Alternatively, instead of, or in addition to the oncogene, a suppresor of a tumor suppresor gene, such as a suppresor/inhibitor of p53, may be used to transform cells. Such suppressors/inhibitors, without limitation, may include various forms of dominant negative form of the TS (tumor suppressor) gene, antisense oligoes, and various RNAi constructs (siRNA, short hairpin RNA etc.), etc.

Furthermore, in certain embodiments, additional genes such as SV40 small t antigens may be introduced into the target cell.

More than one DNA encoding an oncogene or TS gene suppressor can be used in the present method to produce tumorigenic cells. In the embodiments in which two or more oncogene-encoding DNAs are introduced, the DNAs encode oncogenes which function in biochemically distinct manners from one another. For example, each DNA can encode an oncogene that functions in a different biochemical (e.g., signaling) pathway. That is, for example, if two oncogene-encoding DNAs are used, each encodes or activates/enhances expression of an oncogene which functions in a distinct pathway. Any number of oncogene-encoding DNAs can be introduced into normal human somatic cells in which telomerase is ectopically expressed in order to render them tumorigenic. For example, in some instances it is desirable to introduce three, four, five, six or even more oncogene-encoding DNAs. The DNAs can each function in/affect a different signaling pathway or more than one can function in/affect a common pathway.

The two types of DNA introduced in the present method can be obtained from a variety of sources. For example, they can be cloned DNA, DNA obtained from a source in which they occur in nature or DNA produced by synthetic or recombinant DNA methods. They can be cDNA or genomic DNA. They can be introduced into the normal human somatic cells by a variety of techniques, such as by means of an appropriate vector (e.g., a retrovirus, such as an amphotropic retrovirus; an adenovirus vector; lentivirus); calcium phosphate-mediated transfection; lipofection; microinjection; microparticle bombardment; RNA transfection; naked DNA injection or electroporation). The resulting normal human somatic cells contain exogenous DNA encoding telomerase catalytic subunit and exogenous DNA comprising at least one oncogene; expression and/or function of the DNAs results in production of tumorigenic human somatic cells from the parental normal cells. Progeny of such cells are tumorigenic.

In one embodiment, the tumorigenic primary glandular epithelial cell (e.g. BPEC) forms tumors in immuno-compromised mice into which it is introduced, and the tumors formed are invasive and/or metastatic in the mice.

In one embodiment, the invention relates to a tumorigenic primary glandular epithelial cell (e.g. BPEC) produced by introducing into the subject normal primary glandular epithelial cells exogenous DNA comprising: (a) DNA encoding (human) telomerase catalytic subunit; (b) DNA encoding an oncogene (or TS gene suppressor) which functions in a first signaling pathway; and (c) DNA encoding an oncogene (or TS gene suppressor) which functions in a second signaling pathway, wherein the first and the second signaling pathways are not the same and the DNA of (a), the DNA of (b) and the DNA or (c) are stably incorporated into and stably expressed in the subject normal epithelial cell and progeny thereof. The exogenous DNA may be incorporated into genomic DNA of the cells.

In a preferred embodiment, the DNA of (a) is cDNA which encodes hTERT; the DNA of (b) is cDNA that encodes an oncogene that functions in the same signaling pathway as does the ras oncogene product and the DNA of (c) is cDNA that encodes an oncogene that functions in the same signaling pathways as does the SV40 LT-encoded oncoprotein, wherein function of the oncogene encoded by the cDNA of (b) and the oncogene encoded by the cDNA of (c) in their respective signaling pathways in the normal human somatic cells in which human telomerase catalytic subunit is ectopically expressed results in production of tumorigenic primary glandular epithelial cells. For example, the DNA of (b) is cDNA which encodes the H-ras oncogene product and the DNA of (c) is cDNA which encodes the SV40 LT oncogene product (or HPV E6 and E7 products). Such cells may form tumors in immuno-compromised mice into which they are introduced, and the tumors formed may be non-invasive and non-metastatic in the mice.

In certain embodiments, the exogenous DNA additionally may comprise DNA that encodes at least one oncogene in addition to the DNA of (b) and the DNA of (c). Preferably, each additional oncogene encoded by the exogenous DNA functions in a distinct biochemical pathway from the biochemical pathways in which other oncogenes encoded by exogenous DNA expressed in the cell function.

In certain embodiments, the exogenous DNA of (b), the exogenous DNA of (c) or the exogenous DNA of (b) and (c) is DNA that comprises an oncogene characteristic of malignant human tumor cells that develop in humans.

In certain embodiments, the subject modified tumorigenic epithelial cells additionally comprise exogenous DNA whose expression and/or function causes metastasis and/or invasion of the cells in an animal into which they are introduced.

In a related aspect, the invention relates to a method of producing such tumorigenic primary glandular epithelial cells (e.g. BPEC) from the corresponding subject normal primary glandular epithelial cells (e.g. BPEC), comprising introducing into such normal epithelial cells exogenous DNA which, when expressed in the normal epithelial cells, transforms the normal epithelial cells into tumorigenic epithelial cells which grow in an anchorage-independent manner in semi-solid medium and form tumors in immuno-compromised mice into which they are introduced. The invention also contemplates a tumorigenic mammalian glandular epithelial cell produced by such methods.

In one embodiment, at least about 75%, about 85%, or about 90% of such tumorigenic cells are CD44$^+$, ESA$^+$ and CD24$^\pm$, and there is essentially no vimentin expression in such cells. However, upon injection of sufficient amount of such tumorigenic cells into immuno-compromised mice, tumor cells isolated from these xenograph animals give rise to a mixed population of tumor cells with mixed expression of CD44, CD24, ESA, vimentin, E-cadherin, or keratin 18.

In other embodiment, such xenograph tumors arising from the injected tumorigenic cells form glandular structures similar to those seen in human tumors. In other embodiments, such xenograph tumors arising from the injected tumorigenic cells are invasive into adjacent tissues, such as skeletal muscle. In one embodiment, xenograph tumors arising from the injected tumorigenic cells are metastatic, for example, to lung in >95% of the host xenograph animals.

In one embodiment, xenograph tumors arising from the injected tumorigenic cells express progesterone, and/or estrogen receptors, and are responsive to treatment with progesterone and/or estrogen.

In one embodiment, xenograph tumors arising from the injected tumorigenic cells may express testosterone, and are responsive to treatment with testosterone.

These tumorigenic cells derived from the subject primary glandular epithelial cells (e.g. BPEC), or the tumor model established therefrom, may be used in in vitro and/or in vivo methods of identifying a drug or gene or protein or any other treatment that targets tumor cells or their environment locally or systemically which reduces proliferation of tumorigenic epithelial cells. Such method comprises propagating tumorigenic epithelial cells of the invention in the presence of a drug or drug candidate to be assessed for its ability to reduce proliferation of the tumorigenic epithelial cell, under conditions appropriate for the drug to enter the cells; determining the extent to which proliferation of the tumorigenic epithelial cells occurs in the presence of the drug to be assessed and comparing the extent determined with the extent to which proliferation of the tumorigenic epithelial cells occurs under the same conditions, but in the absence of the drug to be assessed, wherein if proliferation occurs to a lesser extent in the presence of the drug to be assessed than in its absence, the drug to be assessed is a drug which reduces proliferation of tumorigenic epithelial cells.

In a related aspect, such tumorigenic epithelial cells may be used in an in vitro method of assessing the ability of a drug or treatment which inhibits proliferation and invasive properties of tumorigenic epithelial cells to assess its ability to inhibit proliferation of such cells to a greater extent than it inhibits proliferation of parental normal epithelial cells, comprising culturing the subject tumorigenic epithelial cells with the drug; determining the extent to which proliferation of the tumorigenic epithelial cells occurs in the presence of the drug and comparing the extent determined with the extent to which proliferation of corresponding normal epithelial cells cultured under the same conditions occurs, wherein if proliferation of tumorigenic epithelial cells occurs to a lesser extent than does proliferation of corresponding normal epithelial cells, the drug inhibits proliferation of tumorigenic epithelial cells to a greater extent than it inhibits proliferation of corresponding normal epithelial cells.

In one embodiment, the tumorigenic cells form a tumor in an immunocomprimised xenographic animal model.

In one embodiment, the tumor is invasive and/or metastatic.

In another related aspect, such tumorigenic epithelial cells may be used in an in vivo method of identifying a drug, treatment or cellular or genetic modification which reduces the proliferation, invasion or metastasis of tumorigenic epithelial cells, comprising introducing the subject tumorigenic epithelial cells into an appropriate animal, in which such cells proliferate and result in formation of a tumor; administering a drug to be assessed for its ability to reduce proliferation of tumorigenic epithelial cells to the animal, referred to as a test animal, and determining whether proliferation of tumor cells is less in the test animal than in a control animal, in which introduction of such cells resulted in formation of a tumor and to which the drug was not administered, wherein if proliferation of tumorigenic epithelial cells is less in the test animal than in the control animal, the drug is a drug which reduces proliferation of tumorigenic epithelial cells in vivo.

The subject tumorigenic epithelial cells can also be used in a method of identifying a drug which selectively inhibits the ras oncogene product, comprising: a) culturing tumorigenic epithelial cells, referred to as a first variety of tumorigenic cells, produced by introducing into genomic DNA of the subject normal epithelial cells DNA comprising: (1) cDNA which encodes human telomerase catalytic subunit; (2)

cDNA which encodes the H-ras oncogene product and (3) cDNA which encodes the SV40 LT oncogene product, thereby transforming the subject normal epithelial cells into tumorigenic human somatic cells, with a drug to be assessed for its ability to inhibit the ras oncogene product; b) culturing tumorigenic epithelial cells, referred to as a second variety of tumorigenic cells, produced by introducing into genomic DNA of normal somatic cells DNA comprising: (1) cDNA which encodes telomerase catalytic subunit; (2) cDNA which encodes an oncogene other than H-ras oncogene product or the SV40 large T antigen oncogene product and (3) cDNA which encodes the SV40 large T antigen oncogene product with the drug to be assessed for its ability to inhibit the ras oncogene product; c) determining the extent to which the drug inhibits proliferation of the first variety of tumorigenic cells and the second variety of tumorigenic cells; d) comparing the extent to which the drug inhibits proliferation of the first variety of tumorigenic cells with the extent to which the drug inhibits proliferation of the second variety of tumorigenic cells, wherein if proliferation of the first variety of tumorigenic cells is inhibited and proliferation of the second variety of tumorigenic cells is not inhibited, the drug is a drug which selectively inhibits the H-ras oncogene product.

The subject tumorigenic epithelial cells can also be used in a method of identifying a gene whose expression in a tumorigenic cell is related to/involved in metastasis of such cells in vivo, comprising: a) introducing a candidate gene into the subject tumorigenic epithelial cells, thereby producing modified tumorigenic epithelial cells; b) introducing the modified tumorigenic epithelial cells into an animal; c) maintaining the animal into which the modified tumorigenic epithelial cells were introduced under conditions appropriate for formation of tumors and metastasis to occur; and d) determining whether metastasis of the modified tumorigenic epithelial cells occurs, wherein, if metastasis occurs, the candidate gene is a gene whose expression in a tumorigenic cell is related to/involved in metastasis of such cells in vivo.

The subject tumorigenic epithelial cells can also be used in a method of identifying a gene whose expression in a tumorigenic cell is related to/involved in invasiveness of such cells in vivo, comprising: a) introducing a candidate gene into the subject tumorigenic epithelial cells, thereby producing modified tumorigenic epithelial cell; b) introducing the modified tumorigenic epithelial cells into an animal; c) maintaining the animal into which the modified tumorigenic epithelial cells were introduced under conditions appropriate for formation of tumors and invasion of the tumor into tissues of the animal to occur; and d) determining whether invasion of the modified tumorigenic epithelial cells occurs, wherein, if invasion occurs, the candidate gene is a gene whose expression in a tumorigenic cell is related to/involved in invasion of such cells in vivo.

The subject tumorigenic epithelial cells can also be used in a method of identifying a gene product which is expressed in tumor cells but not in normal cells of the same type or a gene product which is not expressed in tumor cells but is expressed in normal cells, comprising analyzing the subject tumorigenic epithelial cells expressing exogenous DNA comprising (a) DNA encoding subunit telomerase catalytic; (b) DNA encoding a first oncogene; and (c) DNA encoding a second, distinct oncogene for gene products; analyzing normal parental epithelial cells of which the tumorigenic cells are a variant for gene products and comparing gene products produced by the tumorigenic cells and the normal parental cells, whereby a gene product which is expressed in tumorigenic cells but not in normal parental cells or a gene product which is not expressed in tumorigenic cells but is expressed in normal parental cells is identified, thereby identifying a gene product which is expressed in tumor cells but not in normal cells of the same type or a gene product which is not expressed in tumorigenic cells but is expressed in normal cells of the same type.

The invention also provides an in vitro method of identifying a drug which inhibits or negatively affects one or more characteristics of tumorigenic cells, the characteristics including: cell viability, growth, differentiation, proliferation, invasiveness, ability to metastasize, anchorage-independent growth, angiogenesis, and response to drugs, hormones, peptides, lipids, nucleic acids, radiation, gene expression modifiers, other cells (immune, stromal etc.) the method comprising: (1) propagating tumorigenic cells of the subject invention as described above, in the presence of a candidate drug to be assessed for its ability to inhibit or negatively affect the one or more characteristics of the tumorigenic cells, under conditions appropriate for the drug to enter cells; (2) determining the extent to which the characteristics is inhibited or negatively affected in the presence of the candidate drug to be assessed; and, (3) comparing the extent determined with the characteristics of the tumorigenic cells under the same conditions, but in the absence of the candidate drug to be assessed, wherein if the characteristics is substantially inhibited or negatively affected in the presence of the candidate drug to be assessed than in its absence, the candidate drug to be assessed is a drug which inhibits or negatively affects one or more the characteristics of the tumorigenic cells. In one embodiment, the one or more characteristics is inhibited or negatively affected by at least about 20%, 40%, 50%, 60%, 70%, 80%, 90%, or 100% in the presence of the candidate drug to be assessed than in its absence. In one embodiment, the method further comprises using the identified drug as a lead molecule to identify additional drugs that more potently inhibits or negatively affects the characteristics.

The invention also provides a drug identified by the method of the instant invention.

The invention also provides a pharmaceutical composition comprising an effective amount of the drug so identified, and one or more pharmaceutically acceptable excipient or salt.

The invention also provides an in vitro method of identifying a drug which enhances or positively affects one or more characteristics of tumorigenic cells, the characteristics including: differentiation, apoptosis, sensitivity to chemotherapy/radiotherapy, or senescence, the method comprising: (1) propagating tumorigenic cells of the subject invention, in the presence of a candidate drug to be assessed for its ability to enhance or positively affect the one or more characteristics of the tumorigenic cells, under conditions appropriate for the drug to enter cells; (2) determining the extent to which the characteristics is enhanced or positively affected in the presence of the candidate drug to be assessed; and, (3) comparing the extent determined with the characteristics of the tumorigenic cells under the same conditions, but in the absence of the candidate drug to be assessed, wherein if the characteristics is substantially enhanced or positively affected in the presence of the candidate drug to be assessed than in its absence, the candidate drug to be assessed is a drug which enhances or positively affects one or more the characteristics of the tumorigenic cells.

The invention also provides an in vivo method of identifying a drug which inhibits or negatively affects one or more characteristics of tumor generated by tumorigenic cells in a tumor model, the characteristics including: tumor growth, invasiveness, metastasis, or angiogenesis, the method comprising: (1) introducing to test animals tumorigenic cells of the subject invention to generate tumors; (2) administering a candidate drug to the test animals to assess its ability to inhibit or negatively affect the one or more characteristics of the tumor; and, (3) determining the extent to which the characteristics is inhibited or negatively affected in the presence of the candidate drug; wherein if the characteristics is substantially inhibited or negatively affected in the presence of the candidate drug to be assessed than in its absence, the candidate drug to be assessed is a drug which inhibits or negatively affects one or more the characteristics of the tumor.

The invention also provides a method of identifying a gene whose expression in a tumorigenic cell is related to/involved in metastasis of such cells in vivo, comprising: (1) introducing a candidate gene into tumorigenic cells of the subject invention, thereby producing modified tumorigenic cells; (2) introducing the modified tumorigenic cells to test animals; (3) maintaining the test animals under conditions appropriate for formation of tumors and metastasis to occur; and (4) determining whether metastasis of the modified tumorigenic cells occurs, wherein, if metastasis occurs, the candidate gene is a gene whose expression in a tumorigenic cell is related to/involved in metastasis of such cells in vivo.

The invention also provides a method of identifying a gene whose expression in a tumorigenic cell is related to/involved in invasion of such cells in vivo, comprising: (1) introducing a candidate gene into tumorigenic cells of the subject invention, thereby producing modified tumorigenic cells; (2) introducing the modified tumorigenic cells to test animals; (3) maintaining the test animals under conditions appropriate for formation of tumors and invasion to occur; and (4) determining whether invasion of the modified tumorigenic cells occurs, wherein, if invasion occurs, the candidate gene is a gene whose expression in a tumorigenic cell is related to/involved in invasion of such cells in vivo.

The invention also provides a method of identifying a gene product which is expressed in tumor cells but not in normal or non-tumorigenic cells of the same type, or a gene product which is not expressed in tumor cells but is expressed in normal or non-tumorigenic cells of the same type, comprising: (1) analyzing tumorigenic cells of the subject invention; (2) analyzing normal parental cells of which the tumorigenic cells are a variant for gene products; and, (3) comparing gene products produced by the tumorigenic cells and the normal parental cells, whereby a gene product which is expressed in tumorigenic cells but not in normal parental cells, or a gene product which is not expressed in tumorigenic cells but is expressed in normal parental cells is identified, thereby identifying a gene product which is expressed in tumor cells but not in normal cells of the same type, or a gene product which is not expressed in tumorigenic cells but is expressed in normal cells of the same type.

The invention also contemplates equivalent embodiments in the cancer stem cells, all genetically and otherwise modified derivatives, and metastatic derivatives isolated/purified using the methods and media of the instant invention.

VI. Isolation of Mammary Epithelial Cells:

One embodiment of the invention provides methods to isolate a specific type of glandular epithelial cells—mammary epithelial cells, especially those exhibiting luminal epithelial cell phenotype (e.g. BPEC), although similar procedures may be used for the isolation of other glandular epithelial cells from other tissues.

Taylor-Papadimitriou and Stampfer (Culture of Human Mammary Epithelial Cells, in *Culture of Epithelial Cells*, pp. 107-133, R. Ian Freshney, Ed., Wiley-Liss, Inc., New York, N.Y.) described various procedures and reagents useful for isolation and culturing of human mammary epithelial cells, the entire content of which is incorporated herein by reference.

One source of mammary epithelial cells comes from milk. Early lactation and post-weaning milks give the highest yield of epithelial cells. In a typical protocol for milk collection, 2-7 days postpartum milk (about 5-20 mL per patient) is collected by expressing milks manually into a sterile container. The milks are pooled and diluted 1:1 with RPMI 1640 medium to facilitate centrifugation at 600-1000 g for about 20 minutes. The supernatant is carefully removed without disrupting the cell pellet, which is then washed 2-4 times with RPMI 1640 with 5% FCS until supernatant is not turbid. Resuspend the packed cell volume in growth medium and plate 50 µL packed cells in 5-cm dishes in 6 mL the subject (primary) growth medium. Incubate at 37° C. in 5% $CO_2$. Follow the rest of the subject methods to isolate/subculture glandular epithelial cells.

In an alternative embodiment, mammary epithelial cells can be isolated from reduction mammoplasty tissue, or other surgical procedures. An enzymatic dissociation technique, (modified from Hallowes et al., Cancer Res. 37: 2492-2505, 1977) coupled with crude dissection, yields large amount of pure epithelial tissues from each individual donor.

Human mammary tissue can be obtained as discarded tissues from mammoplasty surgery. Such material (preferably freshly dissected within 1-2 hours, no more than 5 hours) is placed in sterile containers with sterile buffer or Ham's F-12 medium with insulin, antibiotics, and 10% FBS (e.g. 10 µg/mL insulin, 100 U/mL penicillin, 100 µg/mL streptomycin, 50 U/mL polymixin B, and 5 µg/mL fungizone in Ham's F12 medium). If not used immediately as above, tissues can be stored at 4° C. for up to 72 hours.

Transfer cut pieces of the tissue into a Petri dish. Separate the epithelial areas (appear as embedded white strands) from the stromal matrix and the grossly fatty material in sterile 150 mm Petri dishes using a combination of sterile scalpel, forceps, and scissors. Then transfer the minced epithelium-containing tissue into a conical centrifuge tube (50 or 15 mL) with the tissue making up no greater than ⅓ of the volume of the tube. Bring the tube to full volume with tissue digesting medium (final concentration of 150 U/mL collagenase, 100 U/mL hyaluronidase, and 10% FBS in tissue mix medium), leaving only a small air space to allow for gentle mixing during rotation overnight at 37° C. Centrifuge the tubes at 600 g for 5 minutes. Discard the supernatant fat and medium. Optionally, dilute a small volume of the pellet in medium to check for degree of digestion. Digestion is complete when microscopic examination shows clumps of cells (organoids) with ductal, alveolar, or ductal-alveolar structures free from attached stroma. If digestion is incomplete, repeat the digestion for another 4-12 hours until completion. When digestion is complete, centrifuge tubes at 600 g for 5 minutes, carefully aspirate supernatant, and resuspend pellet in tissue mix medium (about 15 mg/50-mL, 5 mL/15-mL). Filter the mixture, a few millileters a time, through a sterile 150 µL pore-size filter, and wash the organoids left on the filter a few times with 2-3 mL of medium. Flip the filter and wash the organoids off into a sterile container to collect the 150 µL organoid pool, which contains mostly ductal structures.

Repeat the same procedure using 95 µL pore-size filter to collect 95 µL organoid pool, which contains mostly smaller ductal and alveolar structures. The filtrate contains mostly small epithelial clumps and stromal cells. Transfer the 150 µL and the 95 µL organoids collections, and the final filtrate to 50-mL tubes and centrifuge at 600 g for 5 minutes. Aspirate the supernatant, resuspend the pellets in each tube by adding 1 mL medium for each 0.1 mL of packed pellet. Transfer the resuspended materials, drop by drop, onto culture surfaces to cover different areas of the dish. Then add the subject primary medium and follow the rest of the protocol.

In yet another embodiment, the tissues are minced down to fragments about 1-2 mm in size, and digested with collagenase in Hank's buffered saline solution (HBSS) at 37° C. overnight. The resulting mixture of organoids that contain organoids which are separated from single cells that are mostly stromal and myoepithelial by three consecutive rounds of centrifugation (5 min. at 200×g, 100×g and 20×g). The pellets and supernatants are collected in six fractions (200 g, 100 g and 20 g) and filtered through a 75 µm mesh, and subsequently a 45 µm mesh. All filtered fractions are plated in Primaria™ tissue culture dishes (or similar mixed-charged surfaces) in the subject culture medium. The cells are grown for 7 days during which medium is changed every day. On day 8 and 9 plates are trypsinized with 0.025% trypsin removing all stromal cells. Epithelial cells are harvested with 0.15% trypsin and transferred to new Primaria™ plates in the subject medium. After one week, cells are transferred to PWI medium and subcultured in the same medium.

In a specific embodiment, small organoids from breast tissues, rather than larger ones, are used as cell sources, since they tend to yield better results than larger ones. While not wishing to be bound by any particular theory, it is possible that smaller organoids come from smaller lobules of the breast tissues, from where about 99% of breast cancers originate, instead of from larger ducts. It is also possible that the smaller organoids from small lobules are biologically distinct from the larger organoids from large ducts.

Fibroblast cell growth is generally not a problem since the subject medium does not support fibroblast cell growth effectively. However, if fibroblast growth is observed, especially in the 150 µL and 95 µL organoid fraction, fibroblasts can be removed by differential trypsinization as follows. When the epithelial patches are large, aspirate medium, wash once with saline-typsin-versene (STV), and then add 0.5 mL STV per 60-mm dish. Leave STV on cells at room temperature for about 1-2 minutes, with continued observation under the microscope. Knock the dish gently. When the fibroblasts are observed to detach while the epithelial cells remain adherent, remove the STV. Wash cells 2-3 times with sterile PBS and refeed with fresh growth medium.

The isolated mammary epithelial cells can be further characterized by immuno-staining using marker protein antibodies. This may be necessary since the breast is a complex tissue with many different cell types whose lineages are not well defined. For example, fibroblast from stromal tissues may be present in the culture. In addition, one or both of the major breast epithelial cells, luminal and basal epithelial cells, could be proliferating in the culture. All these could be further complicated by phenotypic modulation that occurs in culture.

Fortunately, many monoclonal antibodies against various immunological markers have been development over the years to at least partially solve these problems. Such markers can be used not only to define specific phenotypes in vivo, but also to identify phenotypes of cultured cells. Among them, the expression profiles of various epithelial keratins have been extremely useful, since the expression profiles are maintained in culture as compared to in vivo expression profiles.

Specifically, all luminal epithelial cells express keratin 8 and 18 and most express 19, whereas all the basal cells express keratins 5 and 14, and do not express keratins 8 and 18. Keratin 7 is expressed in both cell types throughout the gland and keratin 19 and 14 are also expressed by both cell types in the large ducts, but not in the TDLU (terminal ductal lobular units). Some of the keratin antibodies are listed below in Table III, which also lists antibodies directed to a polymorphic epithelial mucin (PEM) that is expressed by luminal epithelial cells (Burchell et al., 1983; Gendler et al., 1988), to smooth muscle actin, and to CALLA (common leukocytic leukemia antigen), which is specifically expressed by myoepithelial cells.

TABLE III

Monoclonal Ab Useful for Characterizing Cultured Mammary Epithelial Cells

| Antibody | Target Antigen | Reference |
| --- | --- | --- |
| HMFG-1 | Polymorphic | Burchell et al., J. Immunol. 131: 508-513, 1983. |
| HMFG-2 | Epithelial mucin | Burchell et al., J. Immunol. 131: 508-513, 1983. |
| SM-3 | (PEM) | Burchell et al., Cancer Res. 47: 5476-5482, 1987. |
| BA16 | Keratin 19 | Bartek et al., J. Cell. Sci. 75: 17-33, 1985. |
| BA17 | Keratin 19 | Bartek et al., J. Cell. Sci. 75: 17-33, 1985. |
| CO4 | Keratin 18 | Bartek et al., in Abelev (ed.): "Monoclonal Antibodies to Tumor Associated Antigens and Their Clinical Application." Budapest: Akademai Kiado. |
| DA7 | Keratin 18 | Laueroval et al., Hybridoma 7: 495-504, 1988. |
| LE61 | Keratin 18 | Lane, J. Cell. Biol. 92: 665-673, 1982. |
| LL001 | Keratin 14 | Taylor-Papadimitriou and Lane, in Neville M C Daniel C W (eds.) The Mammary Gland." New York: Plenum Publishing Corp. pp. 181-215. |
| 12C8-1 | Keratin 14 | Dairkee et al., Proc. Natl., Acad. Sci. U.S.A. 82: 7409-13, 1985. |
| M20 | Keratin 8 | Van Muijan et al., Exp. Cell. Res. 171: 331-345, 1987. |
| C-15 | Keratin 8 | Bartek, et al., in Lapis K, Eckhardt S (eds.) Molecular Biology and Differentiation of Cancer Cells." Vol. 2, Basel: Karger; Budapest: Akademai Kiado. |
| RCK 105 | Keratin 7 | Ramaekers et al., Exp. Cell. Res. 170: 235-249, 1987. |
| C-18 | Keratin 7 | Bartek, et al., in Lapis K, Eckhardt S (eds.) Molecular Biology and Differentiation of Cancer Cells." Vol. 2, Basel: Karger; Budapest: Akademai Kiado. |
| V9 | Vimentin | Osborn et al., Eu. J. Cell. Biol. 34: 137-143, 1984. |
| FN-3 | Fibronectin | Keen et al, Mol. Biol. Med. 2: 15-27, 1984. |
| A12 | CALLA | Gusterson et al., J. Natl. Cancer Inst. 77: 343-349, 1986. |
| SM1 | α-actin | Skalli et al., J. Cell. Biol. 103: 2787-2796, 1986; Gugliotta et al., J. Histochem. Cytochem. 36: 659-663, 1988. |

The mammary epithelial cells isolated using the subject methods predominantly differentiate into epithelial cells of luminal phenotype in 3-D culture. These cells express typical markers of luminal epithelial cells, as revealed by using the markers described above, and they can be cultured long-term in vitro without losing differentiation potential. Thus these cells are of the characteristics of true breast progenitor epithelial cells (BPEC). The subject BPEC cells can be used to establish a tumor model that recapitulates many aspects of breast ductal carcinoma.

U.S. Patent Application Ser. No. 60/569,005 describes a human mammary breast cancer model HMLER, in which isolated human epithelial cells (usually of basal but not luminal phenotype) are transformed (e.g., with retroviral vectors) with telomerase (e.g., hTERT), SV40 early region genes (Large T and small t antigens), and a ras pathway gene (e.g., H-ras). The HMLER cells, when injected into immunosuppressed mice, are tumorigenic.

Tumors derived from human mammary epithelial cells (HMECs) had an undifferentiated morphology with focal squamous differentiation, were minimally invasive, exhibited little stromal recruitment, and expressed basal cytokeratins (CK14). In contrast, a novel epithelial precursor cell developed ductal adenocarcinomas that were highly invasive, induced stromal desmoplasia, expressed luminal cytokeratins (CK18) and progesterone receptor. Moreover, these tumors were hormone responsive, highly tumorigenic even at 103 cells per injection, and micrometastatic to lung in 100% of mice in 10 weeks after injection.

These results demonstrate the importance of the starting target cell type in determining morphological and biological behavior in epithelial tumors and provide a new genetically defined human breast xenograft cancer model with that mimics many features reminiscent of the most common type of breast cancer.

The HMLER model recapitulates a rare form of human breast cancer of either undifferentiated or squamous differentiation. However, there is no ductal differentiation in the HMLER model, and both estrogen receptor and progesterone receptor expression are negative (i.e. the tumor does not respond to estrogen and progesterone). The tumor is also non-metastatic, with minimal local invasion and stromal recruitment. Thus the HMLER model roughly corresponds to the human basoid/undifferentiated/squamous carcinomas, partly because the human mammary epithelial cells used to establish the HMLER model may not be precursor cells giving rise to ductal carcinoma.

There are at least 17 histological types of human breast cancers, the majority being invasive ductal carcinoma (about 80%), followed by invasive lobular carcinoma (about 10-15%). Histologically, the squamous type represents less than 1% of the human breast cancer.

The instant invention provides a method of isolating mammary epithelial progenitor cells which can grow long-term in the subject chemically-defined medium, and subsequently, under appropriate conditions, differentiate into ductal phenotype (BPEC) while maintaining its 3D polarized luminal cell phenotype.

The subject medium supports growth of isolated glandular epithelial cells, especially the BPEC cells in culture for at least about 4 weeks, 6 weeks, 10 weeks, 12 weeks, 14 weeks, 15 weeks or more without reaching senescence. This corresponds to at least about 15, 20, 25, 30, 35 or more population doubling (PD) without reaching senescence. Similarly isolated cells growing in other media typically reach senescence after about 3 weeks, or 3-15 weeks PD in culture.

The subject medium supports growth of isolated glandular epithelial cells in culture without elevated expression of p53 and p16, which are typically signs of growth under stressed conditions. In contrast, primary cells growing in MEGM medium of Clonetics express elevated levels of p53 and p16.

In addition, isolated BPECs grow in the subject media without expressing detectable levels of vimentin (fibroblast marker) and CK14 (basal epithelial marker). While in MEGM media, prominent CK14 and vimentin expression is observed.

In another aspect, cells that survive in the subject media can differentiate into epithelial cells of luminal phenotype, similar to that observed in ductal carcinoma, but different from those of myoepithelial cells or basal cells. See Table IV below.

TABLE IV

Expression Profiles of Various Breast Cells

|  | CK18 & 19 | Ck14 | Smooth Muscle Actin (SMA) | p63 |
| --- | --- | --- | --- | --- |
| Luminal Cells | + | − | − | − |
| Ductal Carcinoma | + | − | − | −/+ |
| Myoepithelial Cells | − | + | + | + |
| Basal Cells | − | + | − | + |

HMECs express basoid markers p63 and CK14, and some low level luminal markers CK18. In 3D in vitro culture (cells growing on 100% gelled EHS and are overlaid with media with 2% EHS), HMECs differentiate into squamous cells and express squamous specific marker CK10. In contrast, BPECs cultured in 3D form ascini resembling a hollow ball, with polarized E-cadherin and β-catenin expressions, indicating a luminal phenotype.

Using the methods as described in the U.S. Patent Application Ser. No. 60/569,005 the subject BPECs can be similarly transformed by telomerase (e.g. hTERT), SV40 early region (Large T and small t antigens), and a ras pathway gene (e.g. H-ras). The resulting cell line, BPLER, is also tumorigenic in immunosuppressed mice, but has fundamental difference with the HMLER model.

In one respect, the histology of tumors arising from BPLER is very similar, if not identical to human ductal breast carcinoma. There is prominent luminal marker CK18 expression in BPLER cells and tumors. There is also prominent expression of E-cadherin, a marker indicating polarization of cells. Morphology wise, BPLER xenografts form glandular structures similar to those seen in human tumors. BPLER xenografts into mammary fat pads are invasive into adjacent skeletal muscle, and cause a desmoplastic reaction. BPLER xenografts also express progesterone receptors based on immunohistological staining of xenograft tumor samples. In addition, BPLER tumor sizes respond to estrogen treatment, in that xenograft tumors weighed about 70-100% more in estrogen treated animals than in control animals. BPLER tumors spread within the breast tissue of mice, and the multifocal growth is consistent with lymphovascular invasion and spread of tumors.

According to the tumor stem cell model, tumor stem cells are $CD44^+$ $ESA^+$ $CD24^{low}$. The isolated $CD44^+$ $ESA^+$ $CD24^{low}$ BPECs does not express vimentin or keratin when cultured in the subject media. However, in 3D culture, such isolated BPECs can differentiate into cells of luminal phenotypes and are $CD44^+$, $keratin^+$, and $E\text{-}cadherin^+$. This demonstrates that the subject BPECs have maintained their ability to differentiate under appropriate conditions.

Upon transformation of the subject BPECs to generate tumorigenic BPLER, such cells express CD44, ESA, CD24, vimentin, keratin18 at similar levels to BPECs. In xenograft tumors, the BPLER cells express E-cadherin and the characteristic keratin 18 marker, progesterone receptor, BER-Ep4, EMA (keratin 18$^+$, E-cadherin$^+$, CD44$^{+/-}$, CD24$^{+/-}$, vimentin$^{+/-}$), representing a model closely resembling ductal carcinoma. Moreover, the stroma of the tumors express SMA similar to desmoplastic stroma of human tumors.

Another significant difference between BPLER and HMLER cells concerns the number of cells needed to be injected into immunosuppressed animals for tumor formation. As shown in Table V below, as few as 1,000 BPLER cells injected into immunosuppressed mice are sufficient to induce xenograph tumor formation in about 40-50% of the injected animals, while between about 100,000 to 1,000,000 HMLER cells are needed to induce tumor formation in the same proportion of injected animals.

TABLE V

Number of Cells Needed for Effective Tumorigenesis in Immunosuppressed Mice

| HMLER | | BPLER | |
|---|---|---|---|
| $1 \times 10^6$ | 7/9 | $1 \times 10^6$ | 9/9 |
| $1 \times 10^5$ | 2/9 | $1 \times 10^5$ | 9/9 |
| $1 \times 10^4$ | 0/9 | $1 \times 10^4$ | 9/9 |
| $1 \times 10^3$ | — | $1 \times 10^3$ | 7/15 |

EXAMPLES

The following examples are for illustrative purpose only, and should not be construed to be limiting in any respect of the claimed invention.

Example I

Isolation of Primary Cells

1. Tissues are minced down to fragments about 1-2 mm in size, and digested with collagenase in Hank's buffered saline solution (HBSS) at 37° C. overnight.
2. The resulting mixture of organoids that contain glandular cells are separated from single cells that are mostly stromal and myoepithelial by three consecutive rounds of centrifugation (5 min. at 300×g, 100×g and 50×g).
3. The pellets and supernatants are collected in six fractions (300 g, 100 g and 50 g) and filtered through a 75 micrometer (μm) and 45 μm mesh.
4. All filtered fractions are plated in Primaria™ tissue culture dishes in primary culture medium pWI (see below).
5. The cells are grown for 7 days during which medium is changed every day.
6. On day 8 and 9 plates are trypsinized with 0.025% trypsin removing all stromal cells.
7. Epithelial cells are harvested with 0.15% trypsin and transferred to new Primaria™ plates in PWI medium.
8. After one week cells are transferred and subcultured with 0.075% trypsin in the subject medium.

FIG. 1 illustrates that on day 12, while primary organoid cultures result in homogenous uniform colonies in the subject medium (e.g. PWI), there are multiple cell types forming a bi-phasic appearance in MEGM. Moreover, on day 40, cells in the subject medium (e.g. PWI) are small and proliferating, while in MEGM, the cells have the typical flat, enlarged and vacuolated appearance of senescent cells.

Example II

Methods of Preparing the Media

The media disclosed herein can be made fresh every time from their individual components, which are commercially available from a variety of vendors, such as Sigma, Abott Lab., etc.

Alternatively, certain components of the media may be pre-made as high concentration stock solutions, which can be diluted to their final concentrations as listed in the Tables. The stock solutions should be appropriately stored according to the characteristics of the components, including stability at the storage temperature (e.g., liquid nitrogen, −80° C., −20° C., 4° C., room temperature or about 20-25° C., etc.), sensitiveness to light, natural half life in aqueous or organic solution, etc. Some stock solutions should be remade periodically to keep a fresh stock. The following lists at least one way of preparing several exemplary stock solutions. Other equivalent methods and similar (but not identical) concentration of stock solutions may also be used.

EGF (Epidermal Growth Factor) 100 μg/ml Stock:
  Human (or other mammalian) EGF can be obtained from a variety of commercial venders, such as Upstate Biotechnology. To prepare the stock:
1. Retrieve an unopened vial of 100 μg (human) EGF from refrigerator;
2. Make a 0.1 mg/ml solution by adding 1.0 ml sterile distilled water to the vial; mix gently, but well. If necessary, vary the concentration according to the weight in the vial;
3. Aliquot 0.26 ml portions into sterile ampoules properly labeled (such as "hEGF, 'n' X stock, date, ampoule letter, i.e. A,B,C etc.");
4. Optionally, check sterility of each ampoule by adding 3 μl from each ampoule to 1.5 ml media in a 35 mm dish and incubate 3 or 4 days. Check every day for contamination;
5. Store in −20° C. freezer for up to 3 months. Discard stock after 3 months, and make fresh stocks according to steps above.

(Human) Transferrin 10 mg/ml Stock:
  Human (or other mammalian) Transferrin can be obtained from a variety of commercial venders, such as Sigma CAT# T-2252 Siderophilin. To prepare the stock:
1. Dissolve 1000 mg of transferrin into 100 ml distilled water to yield a stock concentration of 10 mg/ml;
2. Filter for sterility through 0.2 μm filter;
3. Aliquot 2.6 ml and 0.30 ml portions into sterile polypropylene tubes or snap-top tubes properly labeled (such as "Transferrin, 'n' x stock, month/year, vial letter, i.e., A,B, C, etc.");
4. Optionally, check sterility by placing 10 μl from each vial into corresponding labeled 35 mm dish with 1.5 ml media, check every day for contamination 4 days.
5. Store at −20 ° C. freezer.

Insulin 1 mg/ml Stock:
  Insulin can be obtained from a variety of commercial venders, such as Sigma CAT # I-5500. To prepare the stock:
1. Dissolve 1 g of insulin powder in 200 ml of 0.005 N HCl (1 ml 1 N HCl with 199 ml of distilled water) by stirring on a magnetic stirrer;
2. When the solution is clear*, add 800 ml of distilled water, to make the final concentration of insulin 1 mg/ml;
3. Sterilize by filtering through a 0.2 μm filter;

4. Label approximately 30 sterile snap-top tubes and enough 50-ml sterile polypropylene tubes with proper label (such as "Insulin, 'n' X stock, month/year"). Aliquot 2.8 ml and 26 ml portions into sterile polypropylene tubes;
5. Store at −20° C.
* If the solution is not clear after a reasonable amount of stirring, add a few more drops of 1 N HCl, (The total [HCl] should not exceed 0.005 N HCl/liter of solution.) When the solution clears, bring up the total volume to 1 liter with distilled water.

O-Phosphoethanolamine (also 'O-Phosphoroethanolamine' and 'O-Phosphorylethanolamine) stock, 0.1 M:

O-Phosphoethanolamine can be obtained from a variety of commercial venders, such as Sigma CAT# P-0503. To prepare the stock:
1. Dissolve 789.5 mg of O-Phosphoethanolamine in 56 ml of MCDB 170 base medium to give a stock concentration of 14.1 mg/ml or 0.1M;
2. Filter through 0.2 μm filter for sterility;
3. Properly label sterile polypropylene tubes (such as "phospoethanoloamine, 'n' X stock, mo./yr, vial letter") and aliquot 5 ml and 0.6 ml portions;
4. Optionally, check sterility by aliquoting 10 μl from each tube into corresponding labeled 35 mm dish with 1.5 ml media. Check every day for four days, repeat if necessary;
5. Store at −20° C.

In addition, the medium of the instant invention may be prepared by adding additional components to commercially available media. For example, to make the subject culture medium, F-12 liquid Nutrient Mixture (Ham) (1×) media (GIBCO Cat. No. 11765-054) can be mixed with M-199 media (such as CAT #: MT 10-060-CV from MediaTech, Inc.) at 50:50 ratio. The mixture can then be supplemented with glutamine, EGF, transferrin, insulin, progesterone, testosterone, 17B-estradiol, o-phosphorylethanolamine, selenious acid, lionleic acid, BSA, triiodothyronine (T3), hydrocortizone, cholera toxin, HEPES, and other components to reach the final concentrations as listed in Table I or II. The medium may also contain antibiotics if desired, such as penicillin and/or streptomycin.

Example III

Comparison of Cell Growth in the Subject Medium and other Media

The distinct advantages of the subject medium become apparent when compared with other media, especially the only commercially available medium on the market (i.e., the MEGM medium), in terms of the ability to support undifferentiated growth of isolated primary cells for substantial population doublings without going into senescence.

Figure 2:
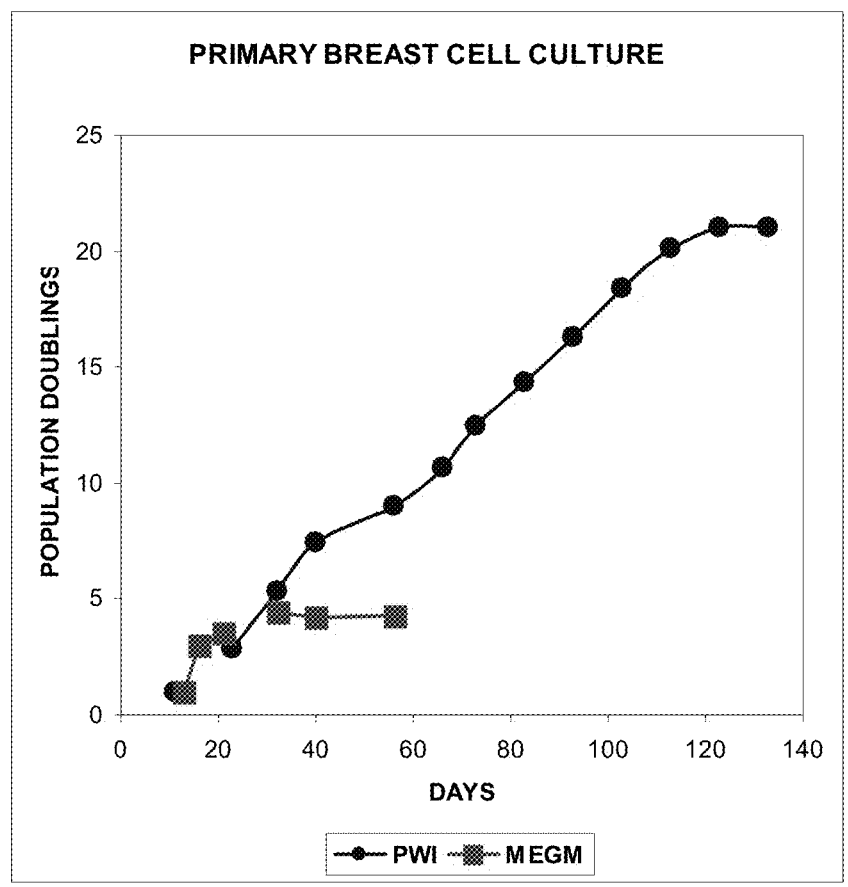
FIG. 2 shows results (growth curve) of identical primary breast cells in the subject medium (e.g. PWI) and one of the tested alternative media for such primary cells—the only commercially available medium MEGM.

FIG. 2 shows a representative result of one of such growth comparison experiments. It shows that primary cells grow in the subject media (e.g., PWI) can proliferate robustly for at least about 4 weeks, or about 15 population doublings, when identical cells from the same donor grow in other media, including the commercially available MEGM media, have largely or completely senesced. At least four types of media were compared to the subject medium. Only the MEGM result was shown, although none of the other tested media fair any better than the MEGM medium. In one typical experiment, growth in the subject medium continued till at least about the $17^{th}$ week, or about 22 population doublings. In contrast, identical cells growing in other media, including MEGM, typically stop at about the $3^{rd}$ week, or about 4 population doublings.

When such cells were transformed by telomerase catalytic subunit by, for example, a retroviral vector, the transformed cells became immortalized, but were not tumorigenic in immuno-compromised xenographic animals (results not shown). Such telomerase-transformed primary cells could continue to grow in the subject media till at least about the $16^{th}$ month, when the experiment was discontinued (results not shown). Once transformed, however, the cells can be grown in medium without certain components, such as agents that induce increased intracellular 3'-5' cyclic adenosine monophosphate (cAMP) levels.

Figure 3:
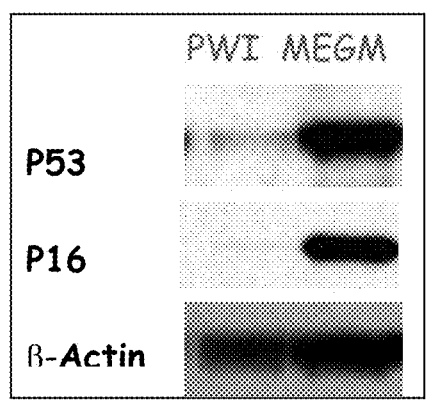
FIG. 3 shows that the isolated primary cells (e.g. primary mammary epithelial progenitors) grow in the subject media (e.g. PWI) relatively stress-free, in that these cells do not express appreciable amount of p53 or p16 gene products. In contrast, similar cells growing in the MEGM medium express large amount of p53 and p16 proteins in Western blot.

FIG. 3 shows that the isolated primary cells (e.g. primary mammary epithelial progenitors) grow in the subject media (e.g., PWI) relatively stress-free, in that these cells do not express appreciable amount of p53 or p16 gene products. In contrast, similar cells growing in MEGM medium express large amount of p53 and p16 proteins in Western blot.

Figure 4:
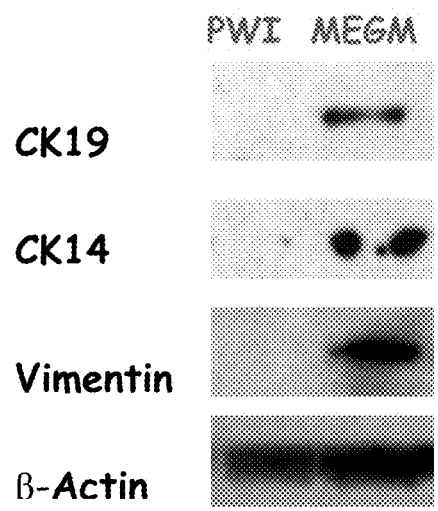
FIG. 4 indicates that the isolated primary mammary epithelial progenitor cells do not express epithelial differentiation markers (such as basal keratin 14 and luminal keratin19) or mesenchymal differentiation markers (such as vimentin) in the subject medium (e.g. PWI), indicating that the population of isolated primary mammary epithelial cells are basically free of contamination by mesenchymal cells, such as fibroblast and other stromal cells. The result also demonstrates that the isolated mammary progenitor cells are growing in an undifferentiated state. In contrast, in the MEGM medium, cells express all these proteins in matched samples.

FIG. 4 indicates that the isolated primary mammary epithelial progenitor cells do not express epithelial differentiation markers (such as basal keratin 14 and luminal keratin19) or mesenchymal differentiation markers (such as vimentin) in the subject media (e.g., PWI). This result indicates that the population of isolated primary mammary epithelial cells are basically free of contamination by mesenchymal cells, such as fibroblast and other stromal cells. The result also demonstrates that the isolated mammary progenitor cells are growing in an undifferentiated state. In contrast, in MEGM media, cells express all these proteins in matched samples.

Example IV

Test Different Ranges of Medium Components for Different Cell Types

The components listed in Table II above are meant to be a general guide for different cell types, thus certain components have a range of suitable concentrations. This Example demonstrates that the concentration of at least certain components of the medium may be varied, sometimes more than 1000-fold, when different cells are cultured.

Three types of cells were used in this experiment: primary breast epithelial progenitors (BEPC) isolated from normal breast tissue; such BEPC cells immortalized by telomerase catalytic subunit (BPE); and such BEPC cells stably transformed by: telomerase catalytic subunit and SV40 early region (or Human Papilloma Virus E6 and E7 genes)—BPLE cells, or telomerase catalytic subunit, SV40 early region (or HPV E6 and E7), and H-ras—BPLER cells.

Using the optimization procedure outlined above, the BEP cells, BPE cells, BPLE cells, and BPLER cells were tested for growth in media with a large variation of concentrations for a number of components. The Table below lists representative results of such a test.

| Components (mg/L) | Organoids Primary Cells (BEPC) PWI + MEDIUM | Primary Cells + telomerase (BPE) PWI MEDIUM | Transformed Cells (BPLE and BPLER) WIT MEDIUM |
|---|---|---|---|
| Hypoxanthine Na | 13.6 | 13.6 | 2.585 |
| Alpha-tocopherol acetate | 2 | 2 | 0 |
| Glutathione (reduced) | 1 | 1 | 0.025 |
| 17 beta estradiol | 0.0034 | 0.0034 | 0.00034 |
| Epidermal Growth Factor | 0.010 | 0.001 | 0.0005 |

| Components (mg/L) | Organoids Primary Cells (BEPC) PWI + MEDIUM | Primary Cells + telomerase (BPE) PWI MEDIUM | Transformed Cells (BPLE and BPLER) WIT MEDIUM |
|---|---|---|---|
| Hydrocortisone | 0.1000 | 0.0010 | 0.00043 |
| D-Glucose | 1000 | 1000 | 2000 |
| Cholera toxin | 0.1 | 0.025 | 0 |
| Insulin | 20 | 10 | 10 |

Compared to BEPC cells, it is evident that BPLE and BPLER cells (tumorigenic) need much less of the most of the tested compositions, with the exception of a 2-fold increase in D-Glucose. In the extreme cases, the BPLE and BPLER cells can grow without any alpha-tocopherol acetate and cholera toxin. Among the other components, the largest decrease is hydrocortisone, where a 1163-fold decrease was measured. Most other components were reduced between 1-50 folds.

In contrast, the telomerase-expressing, immortal but not tumorigenic BPE cells require essentially the same medium as the parental BEPC cells, with a large decrease in hydrocortisone (500-fold), and relatively mild decreases in cholera toxin (4-fold decrease) and EGF (about 7-fold decrease).

The same experimental procedures can be used to optimize medium compositions for other cell types, even outside the range specified in Table II.

Example V

Figure 5:
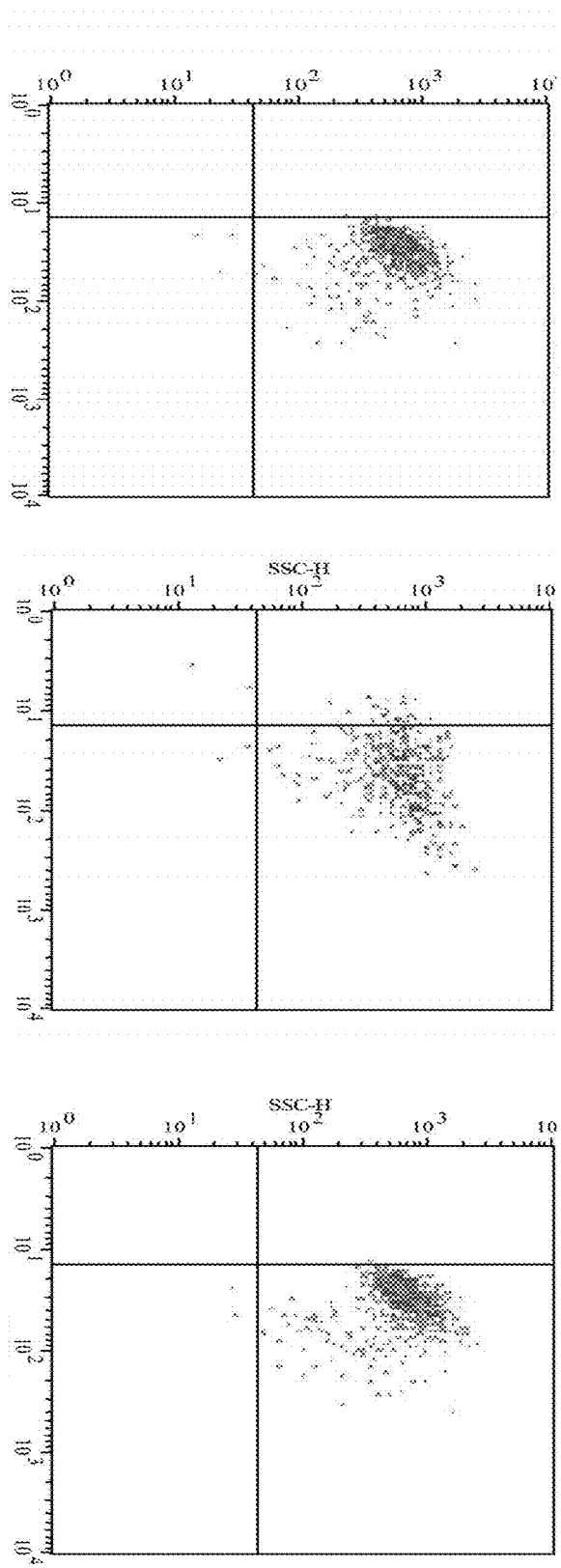
FIG. 5 shows expression profiles of CD44, CD24, and ESA in isolated primary mammary epithelial progenitors cultured in the subject medium.

CD44 and CD24 Expression Profile in Cultured Primary Mammary Epithelial Progenitors It is evident that above 85% (typically above 88%) of the isolated primary mammary epithelial progenitors expressed CD44, CD24, and Epithelial Surface Antigen (ESA). See one typical FACS analysis result shown in FIG. 5. This molecular profile is identical to breast cancer stem cells isolated from human tumor samples.

Example VI

Figure 6:
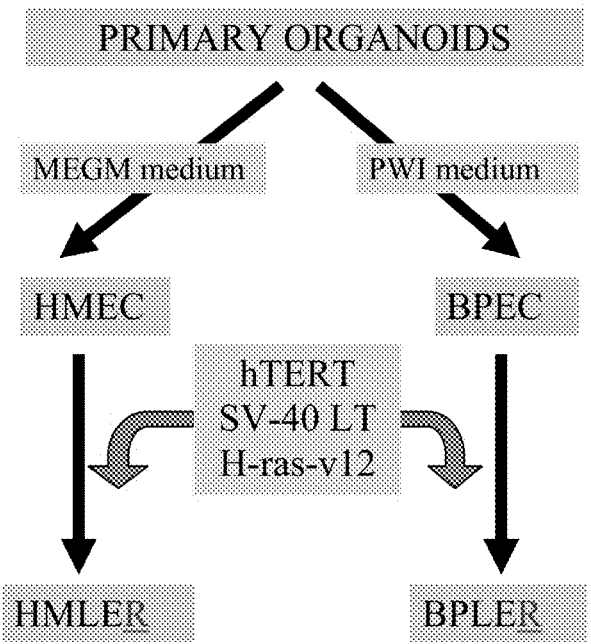
FIG. 6 is a schematic drawing showing the transformation of primary mammary epithelial progenitors to stem cell-like tumorigenic cells.

Transformation of Primary Mammary Epithelial Progenitors to Stem Cell-Like Tumorigenic Cells FIG. 6 is a schematic drawing showing the general steps that may be used to transform primary mammary epithelial progenitors isolated using the subject medium and methods, into stem cell-like tumorigenic cells. In one particular example, primary breast cells (BPEC) grown in the subject medium (e.g. PWI) were infected successively with replication defective amphotropic retroviruses generated from Maloney-based expression constructs, each encoding a distinctive selection marker. To generate these viruses, 293T cells were transfected with 2 µg each of the amphotropic packaging plasmid pCL-10A1 and a retroviral construct expressing a desired gene. The retroviral constructs were in order of infection: a) pMIG-hTERT; expressing catalytic subunit of human telomerase and green-fluorescent protein gfp, b) pBabe-zeo-SVER; expressing SV40 early region (LT-Ag and st-Ag) and zeomycin resistance gene, and, c) pBabe-Ras-puro; expressing oncogenic H-rasV 12 and puromycin resistance gene. Viral supernatants were harvested and used to infect BPECs with 8 µg/ml polybrene. Drug selection was performed by using 100 µg/ml zeocin and 0.25 µg/ml puromycin. The tumorigenic BPLER cells are grown in WIT medium.

Primary breast cells (HMECs) from the same patient cultured in the modified MCDB-170 medium (MEGM; the standard available medium for breast cells) were infected with the same plasmids. The resulting tumorigenic cells are refered to as HMLER. The generation of cells is illustrated in the figure below.

| Cell Name | Genotype | | | Tumorigenicty |
|---|---|---|---|---|
| BPEC | | | | 0 |
| BPE | hTERT | | | 0 |
| BPLE | hTERT | SV40-LT/st | | 0 |
| BPLER | hTERT | SV40-LT/st | H-ras-V12 | 100% |

Subcutaneous tumorigenicity was tested in 6-8 week old immunocompromised athymic nude mice by injecting about $1 \times 10^6$ cells resuspended in 100 µl of 50% matrigel (EHSS). Nude mice were irradiated with 400 rad 12 hr prior to injections. Orthotopic tumorigenicity was tested by injecting about $1 \times 10^6$ cells into the mammary fat pad of Nod/Skid mice. All mice were sacrificed on day 70. Both orthotopic and subcutaneous injections developed tumors 100% of the time within 50 days. In total over 20 mice in each group have been tested for tumorigenicity in three separate experiments.

The table below shows that the tumorigenic BPLER cells of the invention are much more potent than HMLER cells in terms of tumorigenesis. HMLER cells reliably generate tumor in xenographic animal models only when more than $1 \times 10^6$ cells are injected into each animal. At $1 \times 10^5$ cells/animal, less than half of the animals actually develop tumor. There was not a single observed tumors in all 9 experimental animals when only $1 \times 10^4$ tumorigeniccells were used.

In contrast, $1 \times 10^4$ BPLER cells generates tumors in 100% of the experimental animals. In fact, with 10-fold lesser tumorigenic BPLER cells ($1 \times 10^3$ cells/animal), about 50% of the animals still develop tumor. Thus the BPLER cells are at least about 1000-fold more potent than HMLER cells in tumorigenesis.

| HMLER | | BPLER | |
|---|---|---|---|
| $1 \times 10^6$ | 7/9 | $1 \times 10^6$ | 9/9 |
| $1 \times 10^5$ | 2/9 | $1 \times 10^5$ | 9/9 |
| $1 \times 10^4$ | 0/9 | $1 \times 10^4$ | 9/9 |
| $1 \times 10^3$ | — | $1 \times 10^3$ | 7/15 |

Example VII

Characterization of Tumors Generated by Transformed Stem Cell-Like Tumorigenic Primary Mammary Epithelial Progenitors A series of experiments were conducted to characterize the tumors formed by those transformed stem cell-like tumorigenic primary mammary epithelial progenitors.

Figure 7:
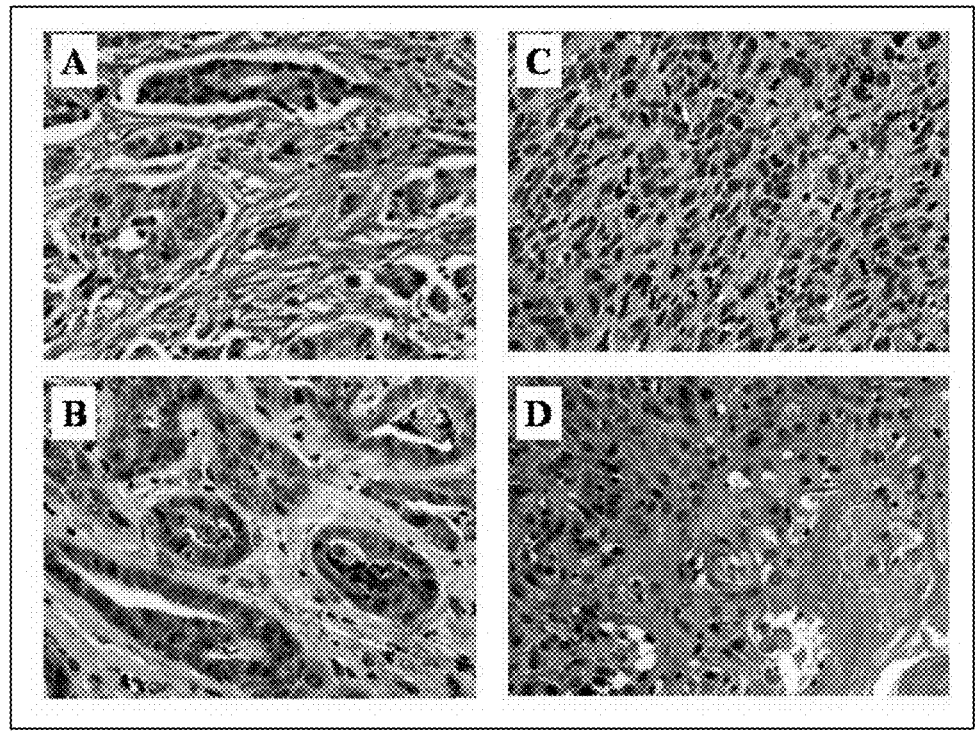
FIG. 7 is microscopic examination of the tumors showing that BPLER tumors recapitulate glandular structures (b) similar to Invasive Ductal Carcinoma of the breast from a human tumor sample (a). In contrast, HMLER tumors were either undifferentiated (c) due to complete lack of ductal structures or clear epithelial morphology; or focally Squamous Carcinomas due to presence of extracellular keratinization (d). This indicates that the subject tumor model is a close approximation of clinical tumor.

In a first experiment, tumors generated by transformed stem cell-like tumorigenic primary mammalian epithelial progenitors were excised from the animals after the animals were sacrificed. Microscopic examination of the tumors show that BPLER tumors recapitulate glandular structures (FIG. 7b) similar to Invasive Ductal Carcinoma of the breast from a human tumor sample (FIG. 7a). In contrast, HMLER tumors were either undifferentiated (FIG. 7c) due to complete lack of ductal structures or clear epithelial morphology; or focally Squamous Carcinomas due to presence of extracellular keratinization (FIG. 7d). This indicates that the subject tumor model is a close approximation of clinical tumor.

Figure 8:
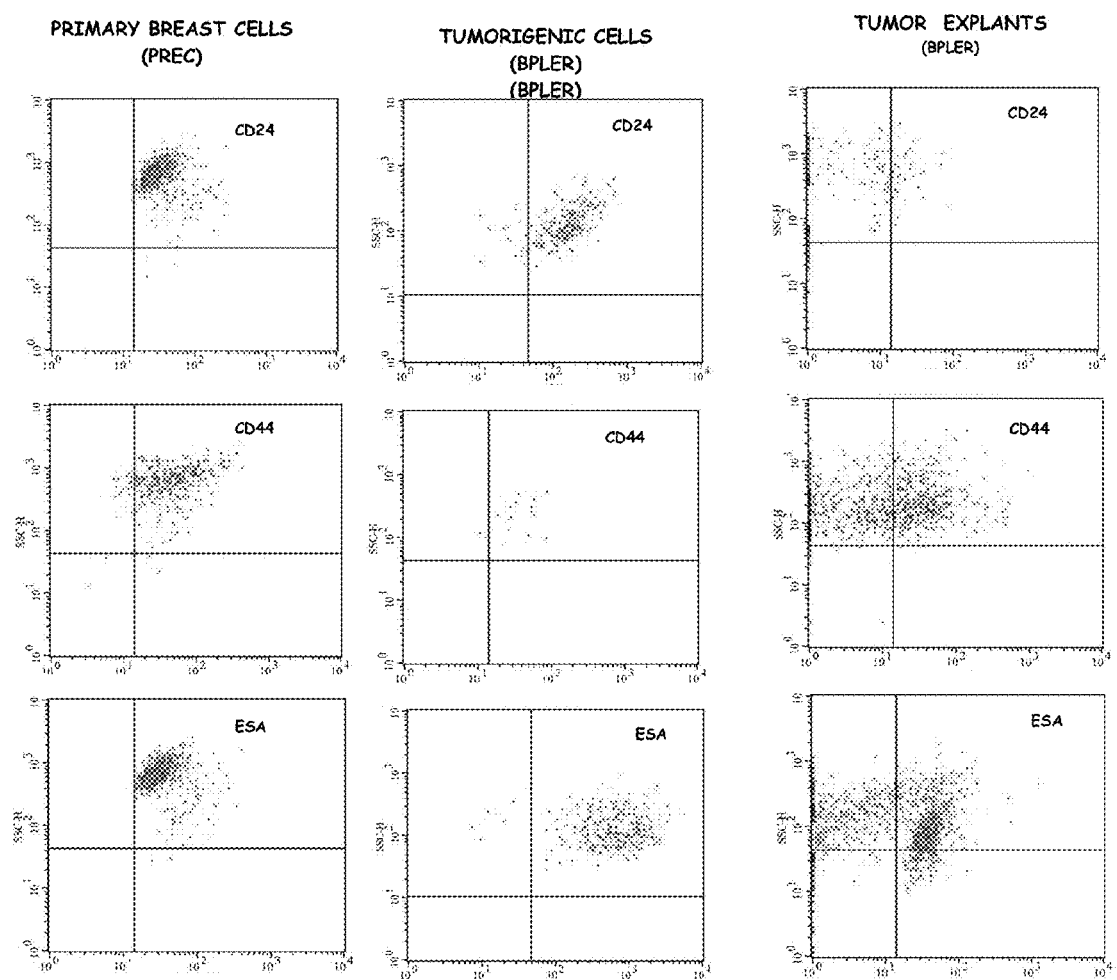
FIG. 8 is FACS analysis of CD44, CD24 and ESA expression on isolated primary breast cells, tumorigenic cells BPLER, and cells from tumor explants generated from implanted BPLER cells. The results indicate that the subject tumor model can recreate in the subject tumor model the breast cancer stem cell marker expression pattern both in vitro and in vivo.

To determine the expression of certain cell-surface antigens, BPLER tumors were isolated from mice, minced and digested into single cells with collagenase (as described for breast organoids above). The single cells from the tumors were incubated with human specific antibodies such as APC-congugated CD24 Ab, PE-congugated CD44 Ab, ESA Ab, and control antibodies. Since only the tumor cells are green fluorescent protein positive, they can be easily identified by FACS. The expression of CD24, CD44 and ESA were analyzed by FACS. The primary breast cells and BPLER cells in tissue culture are homogenous in their expression of all three markers with over 90% of cells expressing CD44, CD24 and ESA. In contrast, the tumor explants exhibited a mixed phenotype of CD44, ESA, and CD24 expression (FIG. 8). This is consistent with the notion that the original tumorigenic cells are stem cell-like, in that they not only "regenerate" themselves ($CD44^+,ESA^+,CD24^{low}$) during the process of tumorigenesis, but also generates less-tumorigenic $CD44^-,ESA^-,CD24^{high}$) tumor cells. This indicates that the subject tumor model can recreate in the subject tumor model the breast cancer stem cell marker expression pattern both in vitro and in vivo. Moreover, this pattern is not merely the product of the genetic manipulation of the normal cells that were isolated, since the expression pattern is already present in primary cells. Therefore, the property of "sternness" resides with the original cell population that has been isolated and expanded in the subject medium, rather than any genetic manipulation of the cells. Moreover, while previous results from human tumors were able to identify the expression pattern of the tumor stem cells, they were not able to address whether this pattern preceded the malignant transformation, or it was acquired during transformation. The results of the subject tumor model identify BPEC cells as the likely normal target cells that give rise to human breast cancer stem cells by virtue of their identical CD44, ESA, CD24 expression to tumor stem cells.

The explanted BPLER tumor cells were FACS sorted into CD24+ and CD24- fractions and re-injected into nude mice. If the BPLER tumor stem cell marker expression were to be functional in these cells, only CD24- fraction would be tumorigenic. The table below shows the results of such an experiment with BPLER tumor explants that confirms this prediction. Therefore, subject tumor model not only recapitulates the breast cancer stem cell marker expression pattern, but also has its functional properties in creating tumorigenic and non-tumorigenic populations in vivo.

| Number of cells injected | CD24 negative cells | CD24 positive cells |
| --- | --- | --- |
| $1 \times 10^3$ | 5/15 | 0/12 |
| $1 \times 10^4$ | 8/15 | 0/6 |

Figure 9:
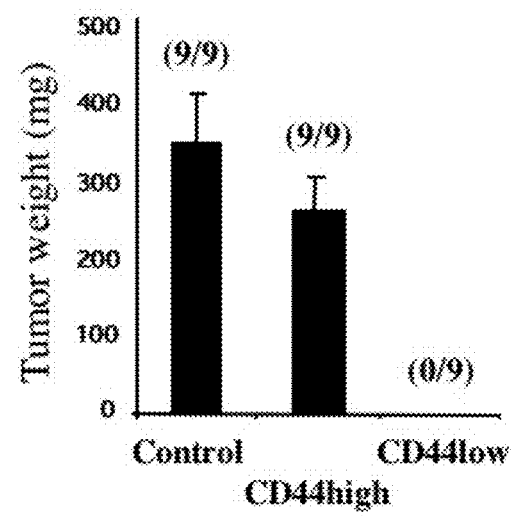
FIG. 9 demonstrates that only $CD44^{high}$ cells induced tumor formation in immuno-compromised host animals, while $CD44^{low}$ cells failed to induce tumor formation.

In vitro, there is at least a 10-fold difference in CD44 expression in BPLER cells. By cell sorting using, for example, FACS, cells falling within the top 20 percentile of all CD44-expressing cells ($CD44^{high}$) and the remaining $CD44^{low}$ cell fractions were separately injected into nude atyhmic mice. As expected from the human tumor data, only $CD44^{high}$ cells induced tumor formation in immunocompromised host animals (see FIG. 9), while $CD44^{low}$ cells failed to induce tumor formation. Since these cells were only expanded in tissue culture these results suggest that tumor stem cell-like properties are present already during in vitro cultivation and not limited to in vivo growth.

Figure 10:
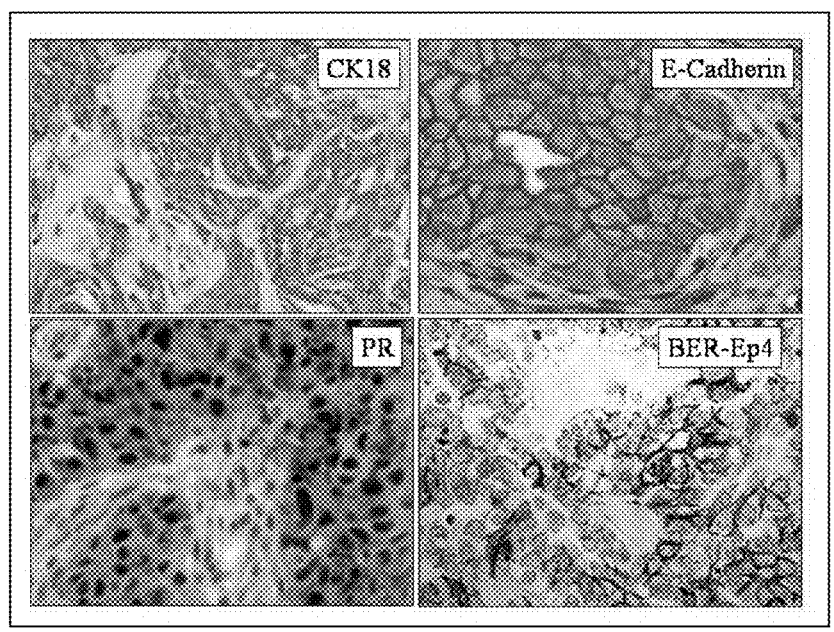
FIG. 10 Immunohistochemical characterization of the subject tumor model show that the tumor cells express breast cancer specific genes; keratin 18 (breast luminal marker), E-cadherin (epithelial marker), progesterone receptor and BER-Ep4 (marker that is positive in adenocarcinomas and negative in squamous carcinomas).

Immunohistochemical characterization of the subject tumor model show that the tumor cells express breast cancer specific genes; keratin 18 (breast luminal marker), E-cadherin (epithelial marker), progesterone receptor and BER-Ep4 (marker that is positive in adenocarcinomas and negative in squamous carcinomas). See FIG. 10. Expression of CK18 and BER-Ep4 both confirm the adenocarcinoma features and exclude a squamous tumor. E-cadherin excludes a mesenchymal tumor. BPLER xenografts express progesterone receptor, which is consistent with the notion that BPLER xenografts are hormone-responsive. This was confirmed by experiments in which estrogen-progesterone treatment of mice increased subject tumor size approximately two-fold compared to untreated mice. In addition, treatment of BPEC, BPE, and BPLE cells with a specific estrogen-antagonist ICI 182,780 resulted in >80% growth inhibitions in vitro (data not shown). Similar tumor xenografts from cells cultured in the MEGM media was negative for progesterone receptor expression and the in vitro growth inhibition of the cells with ICI 182,780 was less than 20% (data not shown).

Figure 11:
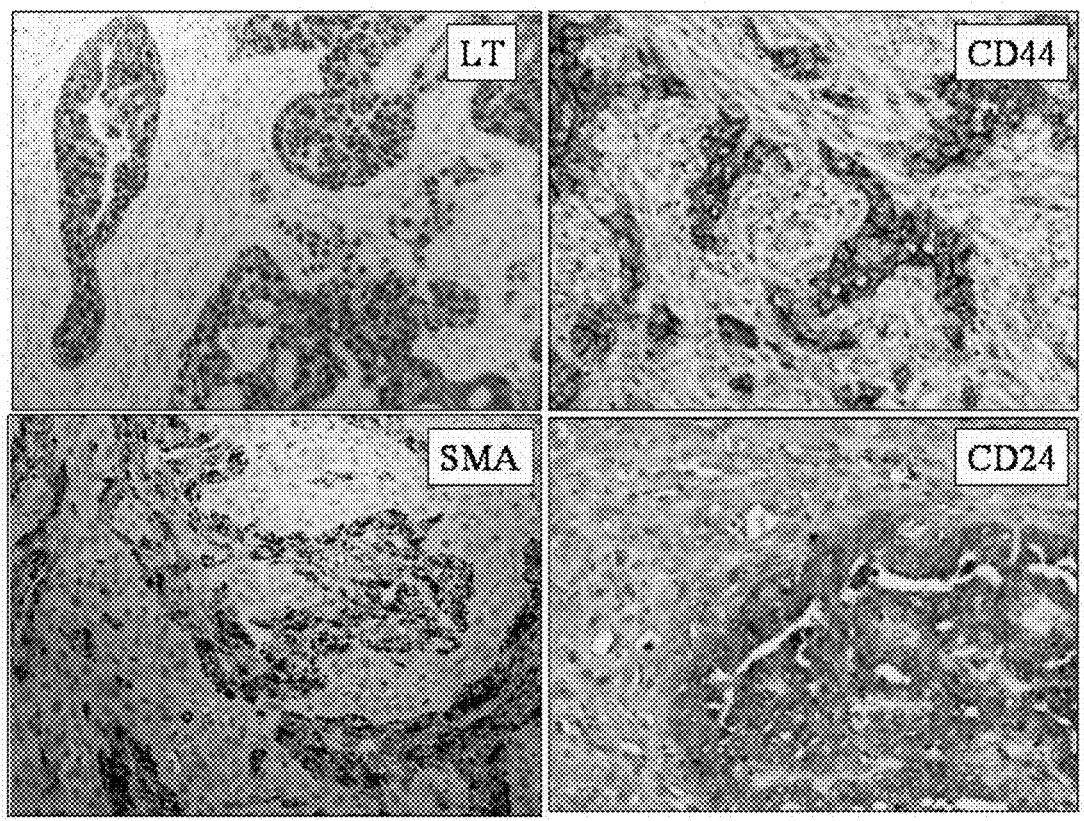
FIG. 11 Immunohistochemical analysis demonstrates that the subject tumor model mimics human breast tumors in every respect very closely, both at the morphologic and molecular level.

Staining with Large T Ag (LT) highlights the glandular morphology and presence of abundant stromal cells that are recruited to the tumor which are smooth muscle actin (SMA) positive, another tpical feature of human breast cancers. CD44 and CD24 immunostains confirm the pattern seen in FACS analysis of the same tumors and show a spectrum of staining intensity (FIG. 11). These immunostains overall demonstrate that the subject tumor model mimics human breast tumors in every respect very closely both at the morphologic and molecular level.

Figure 12:
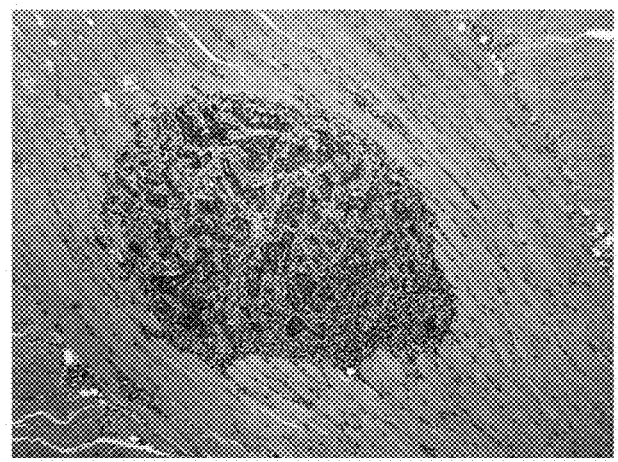
FIG. 12 indicates that BPLER xenographs into mammary fat pads are invasive into adjacent skeletal muscle, and causes a desmoplastic reaction.

FIG. 12 indicates that BPLER xenographs into mammary fat pads are invasive into adjacent skeletal muscle, and causes a desmoplastic reaction. Thus, just like clinical tumors, the BPLER tumors are invasive, a feature selom seen in HMLER tumors.

Figure 13:
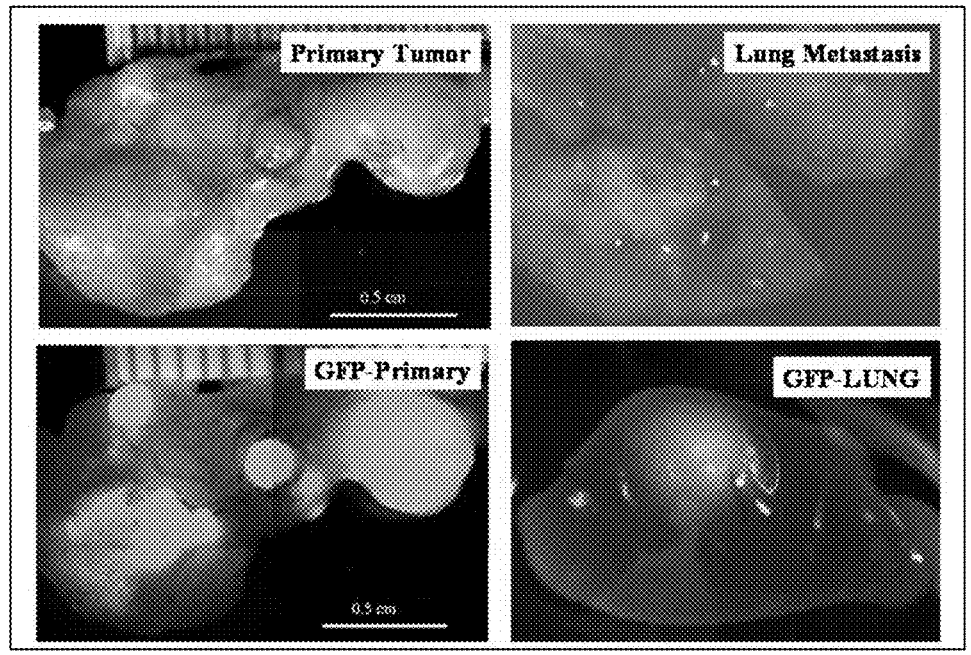
FIG. 13 shows multifocal growth in BPLER xenografts.

Consistent with the invasive behavior in FIG. 12, multifocal growth is observed in BPLER xenografts (FIG. 13). The $GFP^+$ tumor cells were injected into the mammary fat pat of Nod/skid mice and tumors were harvested at 8 weeks. The GFP image highlights that the tumor spread in the fat pad forming discontinuous and separate nodules, which was also confirmed by microscopic examinations of H&E stains (data not shown), consistent with lymphovascular invasion and spread of the tumor. This type of spread pattern is not present in HMLER tumors that grow as a single nodule (data not shown). Moreover, when lungs of the same animals are examined numerous micro-metastatic nodules were identified in 16 out of 18 mice confirming high metastatic potential of the subject tumor model. In one case the metastatic nodule was macroscopic. The lung metastasis was also confirmed microscopically in H&E stains (data not shown).

Example VIII

Differentiation of Isolated Primary Mammary Epithelial Progenitors to Luminal Epithelial Cells Isolated primary mammary epithelial progenitors may be induced to differentiate into luminal epithelial cells in 3D culture.

Figure 14:
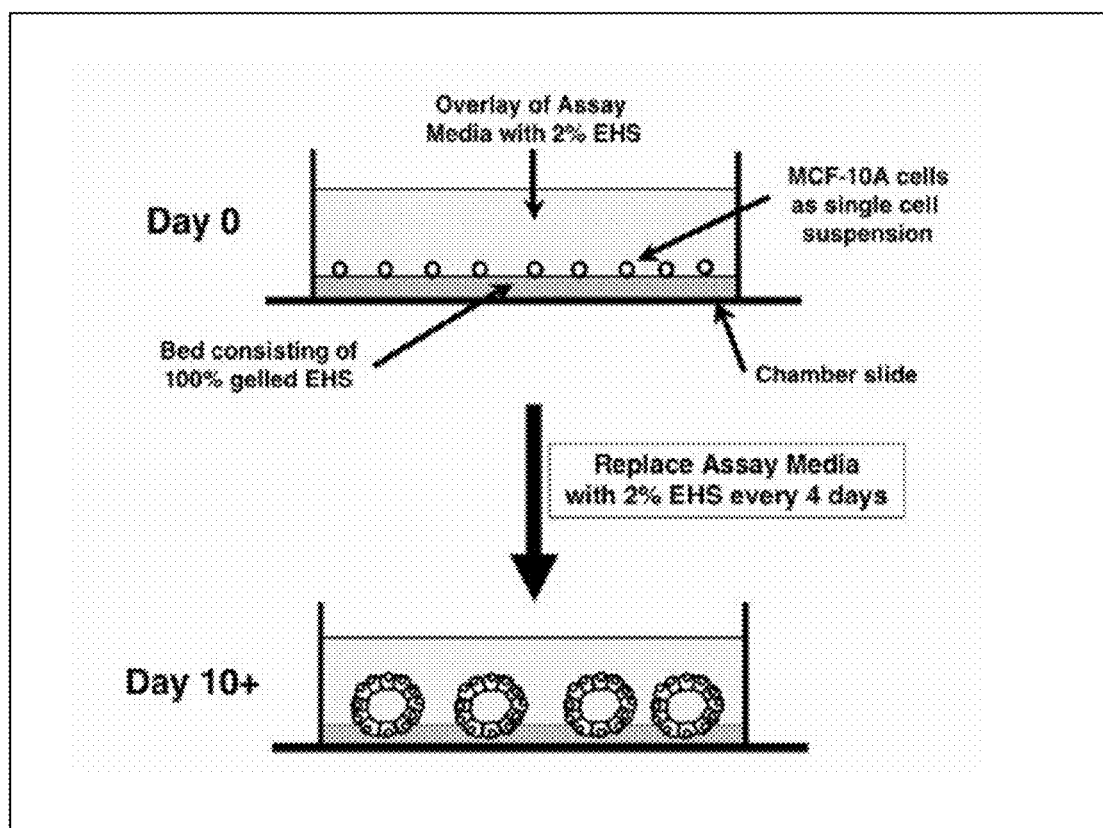
FIG. 14 is a schematic drawing of the 3D culturing methods (adapted from Debnath et al., Methods. 30(3): 256-268, 2003).

FIG. 14 (adapted from Debnath et al., Methods. 30(3): 256-268, 2003) is a schematic drawing of the 3D culturing methods. Briefly, cells to be differentiated are plated at appropriate (low) density on a bed consisting of 100% gelled EHS. A medium with about 2% EHS is then laid upon the cells, such that the EHS will eventually sediment on the cells and stimulate their differentiation into hollow ball-like structures (acini). Such structures resemble the lumen of epithelial ducts in breast.

Figure 15:
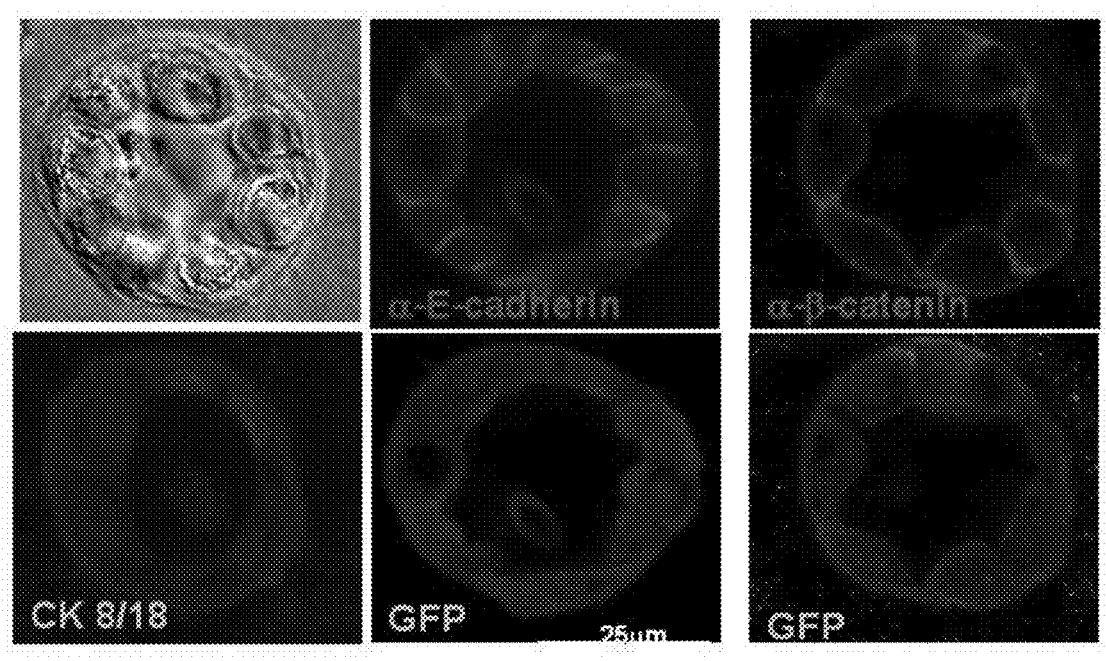
FIG. 15 indicates that primary mammary epithelial progenitors isolated using the subject media may be differentiated in 3D culture, and the developed acini express luminal epithelial cell markers E-cadherin and beta-catenin. Other luminal epithelial cell markers, keratins 8 and 18, are also expressed.

Acini may be fixed and stained to show expression of certain epithelial cell differentiation markers, such as E-cadherin and beta-catenin. FIG. 15 indicates that primary mammary epithelial progenitors isolated using the subject media may be differentiated in 3D culture, and the developed acini express luminal epithelial cell markers E-cadherin and beta-catenin. Other luminal epithelial cell markers, keratins 8 and 18, are also expressed (FIG. 15).

These results demonstrated that the isolated primary mammary epithelial progenitors, when induced to differentiate in 3-D culture, could properly differentiate into epithelial cells of luminal (but not basoid) phenotype, which cells are more similar to the cells the majority of human carcinomas arise. Thus such a tumor model is biologically more relevant to the real disease in human.

REFERENCES

1. *Epithelial cell culture protocols.* edited by Clare Wise. Totowa, N.J.: Humana Press, c2002.
2. Bocker W, Moll R, Poremba C, Holland R, Van Diest P J, Dervan P, Burger H, Wai D, Ina Diallo R, Brandt B, Herbst H, Schmidt A, Lerch M M, Buchwallow I B. Common adult stem cells in the human breast give rise to glandular and myoepithelial cell lineages: a new cell biological concept. *Lab Invest,* 82(6): 737-46, 2002.
3. http://www.cambrex.com/CatNav.catorg.17100.oid.692.navpath.411.prodoid.Mammedia http://www.cambrex.com/RelatedCatNav.catorg.17100.oid.534.prodoid.HMEC.
4. http://www.lbl.gov/LBL-Programs/mrgs/review.html#a4.
5. Speirs V, Green A R, Walton D S, Kerin M J, Fox J N, Carleton P J, Desai S B, Atkin S L. Short-term primary culture of epithelial cells derived from human breast tumors. *Br J Cancer* 78(11): 1421-9, 1998.
6. Stingl J, Eaves C J, Zandieh I, Emerman J T. Characterization of bipotent mammary epithelial progenitor cells in normal adult human breast tissue. *Breast Cancer Res Treat.* 67(2): 93-109, 2001.
7. Gudjonsson T, Villadsen R, Nielsen H L, Ronnov-Jessen L, Bissell M J, Petersen O W. Isolation, immortalization, and characterization of a human breast epithelial cell line with stem cell properties. *Genes Dev.* 16(6): 693-706, 2002.
8. Pechoux C, Gudjonsson T, Ronnov-Jessen L, Bissell M J, Petersen O W. Human mammary luminal epithelial cells contain progenitors to myoepithelial cells. *Dev Biol.* 206 (1): 88-99, 1999.
9. Wagner K U, Boulanger C A, Henry M D, Sgagias M, Hennighausen L, Smith G H. An adjunct mammary epithelial cell population in parous females: its role in functional adaptation and tissue renewal. *Development* 129(6): 1377-86, 2002.
10. Stampfer M R, Yaswen P. Culture systems for study of human mammary epithelial cell proliferation, differentiation and transformation. *Cancer Surv.* 18: 7-34, 1993.
11. Matouskova E, Dudorkinova D, Krasna L, Vesely P. Temporal in vitro expansion of the luminal lineage of human mammary epithelial cells achieved with the 3T3 feeder layer technique. *Breast Cancer Res Treat.* 60(3): 241-9, 2000.
12. Elenbaas B, Spirio L, Koerner F, Fleming M D, Zimonjic D B, Donaher J L, Popescu N C, Hahn W C, Weinberg R A. Human breast cancer cells generated by oncogenic transformation of primary mammary epithelial cells. *Genes Dev.* 15(1): 50-65, 2001.
13. Sherley J L. Asymmetric cell kinetics genes: the key to expansion of adult stem cells in culture. Stem Cells. 2002; 20(6):561-72.
14. Sherley J L, Stadler P B, Johnson D R. Expression of the wild-type p53 antioncogene induces guanine nucleotide-dependent stem cell division kinetics.Proc Natl Acad Sci U S A. 1995 Jan 3.; 92(1):136-40.
15. Rambhatla L, Bohn S A, Stadler P B, Boyd J T, Coss R A, Sherley J L. Cellular Senescence: Ex Vivo p53-Dependent Asymmetric Cell Kinetics. J Biomed Biotechnol. 2001; 1(1):28-37.
16. Lee H S, Crane G G, Merok J R, Tunstead J R, Hatch N L, Panchalingam K, Powers M J, Griffith L G, Sherley J L. Clonal expansion of adult rat hepatic stem cell lines by suppression of asymmetric cell kinetics (SACK). Biotechnol Bioeng. 2003 Sep. 30; 83(7):760-71.
17. Lundberg A S, Randell S H, Stewart S A, Elenbaas B, Hartwell K A, Brooks M W, Fleming M D, Olsen J C, Miller S W, Weinberg R A, Hahn W C. Immortalization and transformation of primary human airway epithelial cells by gene transfer. Oncogene. 21(29):4577-86, 2002.
18. J. Liu, G. Yang, J. A. Thompson-Lanza, A. Glassman, K. Hayes, A. Patterson, R. T. Marquez, N. Auersperg, Y. Yu, W. C. Hahn, G. B. Mills, and R. C. Bast Jr. A Genetically Defined Model for Human Ovarian Cancer Cancer Res., 64(5): 1655-1663, 2004.
19. Rangarajan A, Hong S J, Gifford A, Weinberg R A. Species- and cell type-specific requirements for cellular transformation. Cancer Cell. 6(2):171-83, 2004.

All cited references, US and foreign patents or patent publications, are incorporated herein by reference.

What is claimed is:

1. A method for culturing and maintenance of mammalian hormone-responsive tumorigenic, transformed primary cells, the method comprising:
    (i) isolating normal primary cells from a mammal;
    (ii) introducing into isolated normal primary cells produced in (i) exogenous DNA which, when expressed in the isolated cells, transforms the cells into tumorigenic cells which form tumors in immunocompromised mice into which they are introduced; and
    (ii) culturing and subculturing the tumorigenic cells of (ii) in culture medium comprising:
        (a) vitamin A, vitamin C, and vitamin D;
        (b) Zn, Mg, and Cu;
        (c) transferrin;
        (d) selenium;
        (e) cholesterol, linoleic acid, and lipoic acid;
        (f) hydrocortisone and estrogen;
        (g) triiodothyronine;
        (h) a carrier protein;
        (i) glutathione;
        (j) adenosine triphosphate;
        (k) phosphoethanolamine;
        (l) a nucleotide salvage pathway precursor base selected from the group consisting of hypoxanthine, xanthine, adenine, guanine and thymidine;
        (m) epidermal growth factor; and
        (n) insulin,
    wherein the medium is free of animal serum and tissue extracts and supports undifferentiated growth and/or proliferation of mammalian hormone-responsive tumorigenic, transformed primary cells for at least about 4 weeks or at least about 15 population doubling (PD) in vitro, without a significant decrease in differentiation potential.

2. The method of claim 1, wherein the carrier protein is albumin.

3. The method of claim 1, wherein the estrogen is 17-beta-estradiol.

4. The method of claim 1, wherein said medium also contains vitamin E.

5. The method of claim 1, wherein said medium further comprises adenosine monophosphate.

6. The method of claim 5, wherein the estrogen is 17-beta-estradiol.

7. The method of claim 1, wherein the nucleotide salvage pathway precursor base is xanthine or hypoxanthine.

8. The method of claim 7, wherein the culture medium comprises xanthine and hypoxanthine.

9. The method of claim 1, further comprising at least one of vitamin K3, niacin, or niacinamide.

10. The method of claim 1, wherein the culture medium further comprises an agent that increases intracellular cAMP.

11. The method of claim 10, wherein the one or more agents that induce increased cAMP levels comprise cholera toxin.

12. A method for culturing and maintenance of mammalian hormone-responsive primary cells, the method comprising:
   (i) isolating primary cells from a mammal;
   (ii) culturing and subculturing primary cells isolated in (a) in culture medium comprising:
      (a) vitamin A, vitamin C, vitamin D, and vitamin E;
      (b) Zn, Mg, and Cu;
      (c) transferrin;
      (d) selenium;
      (e) cholesterol, linoleic acid, and lipoic acid;
      (f) hydrocortisone and estrogen;
      (g) triiodothyronine;
      (h) a carrier protein;
      (i) glutathione;
      (j) adenosine triphosphate;
      (k) phosphoethanolamine;
      (l) a nucleotide salvage pathway precursor base selected from the group consisting of hypoxanthine, xanthine, adenine, guanine and thymidine;
      (m) epidermal growth factor;
      (n) insulin; and
      (o) one or more agents that induce increased intracellular 3'-5' cyclic adenosine monophosphate (cAMP) levels,
   wherein the medium is free of animal serum and tissue extracts and supports undifferentiated growth and/or proliferation of mammalian hormone-responsive primary cells for at least about 4 weeks or at least about 15 population doubling (PD) in vitro, without a significant decrease in differentiation potential.

13. The method of claim 12, wherein the carrier protein is albumin.

14. The method of claim 12, wherein the one or more agents that induce increased intracellular cAMP levels comprise cholera toxin.

15. The method of claim 12, wherein the estrogen is 17-beta-estradiol.

16. The method of claim 12, wherein said medium further comprises adenosine monophosphate.

17. The method of claim 16, wherein the estrogen is 17-beta-estradiol.

18. The method of claim 12, wherein the nucleotide salvage pathway precursor base is xanthine or hypoxanthine.

19. The method of claim 12, wherein the culture medium comprises xanthine and hypoxanthine.

20. The method of claim 12, further comprising at least one of vitamin K3, niacin, or niacinamide.

* * * * *